(12) United States Patent
Ozawa et al.

(10) Patent No.: US 8,298,276 B2
(45) Date of Patent: Oct. 30, 2012

(54) STENT DELIVERY SYSTEM, STENT PLACEMENT METHOD, AND STENT ATTACHMENT METHOD

(75) Inventors: Keita Ozawa, Tokyo (JP); Junichi Muramatsu, Sagamihara (JP)

(73) Assignee: Olympus Medical Systems Corp., Tokyo (JP)

(*) Notice: Subject to any disclaimer, the term of this patent is extended or adjusted under 35 U.S.C. 154(b) by 703 days.

(21) Appl. No.: 11/949,472

(22) Filed: Dec. 3, 2007

(65) Prior Publication Data
US 2009/0143849 A1 Jun. 4, 2009

(51) Int. Cl.
*A61F 2/06* (2006.01)
(52) U.S. Cl. .................. 623/1.11; 623/1.12; 623/2.11; 606/108
(58) Field of Classification Search .......... 606/108, 606/109; 623/1.11, 1.15, 1.12, 2.11, 1.23; 604/8, 500
See application file for complete search history.

(56) References Cited

U.S. PATENT DOCUMENTS

| | | | | |
|---|---|---|---|---|
| 5,290,295 | A * | 3/1994 | Querals et al. | 623/1.23 |
| 5,474,563 | A * | 12/1995 | Myler et al. | 606/108 |
| 5,514,176 | A * | 5/1996 | Bosley, Jr. | 623/1.15 |
| 5,713,948 | A * | 2/1998 | Uflacker | 623/1.23 |
| 5,817,101 | A * | 10/1998 | Fiedler | 623/1.11 |
| 6,146,415 | A * | 11/2000 | Fitz | 623/1.11 |
| 6,174,305 | B1 * | 1/2001 | Mikus et al. | 604/500 |
| 6,176,873 | B1 * | 1/2001 | Ouchi | 623/1.22 |
| 6,258,098 | B1 * | 7/2001 | Taylor et al. | 606/108 |
| 6,350,278 | B1 * | 2/2002 | Lenker et al. | 623/1.12 |
| 6,589,251 | B2 * | 7/2003 | Yee et al. | 606/108 |
| 6,991,614 | B2 * | 1/2006 | McWeeney et al. | 604/8 |
| 7,749,280 | B2 * | 7/2010 | Rioux et al. | 623/23.66 |
| 8,197,529 | B2 * | 6/2012 | Cully et al. | 623/1.13 |
| 2004/0116996 | A1 * | 6/2004 | Freitag | 623/1.11 |
| 2005/0131515 | A1 | 6/2005 | Cully et al. | |
| 2006/0100531 | A1 * | 5/2006 | Moser | 600/486 |
| 2006/0100688 | A1 * | 5/2006 | Jordan et al. | 623/1.12 |

(Continued)

FOREIGN PATENT DOCUMENTS
DE 198 28 415 A1 1/1999
(Continued)

OTHER PUBLICATIONS

Chinese Office Action dated Feb. 15, 2012 issued in counterpart Chinese Patent Application No. 200810179243.0.

*Primary Examiner* — Corrine M McDermott
*Assistant Examiner* — Todd J Scherbel
(74) *Attorney, Agent, or Firm* — Scully, Scott, Murphy & Presser, P.C.

(57) ABSTRACT

A stent delivery system which is inserted into an endoscope and is for placing a stent inside a body cavity, this stent delivery system being provided with a long pusher catheter which is flexible; a guide catheter which can pass through the lumen of the pusher catheter in a freely advancing and retracting manner; and a stent which is disposed to the front end of the pusher catheter, and has a cylindrical stent main body into which the guide catheter can be inserted, and a grip piece that is attached so as to extend from the main body and consists of a long narrow member that is pliable and can be disposed in the space between the guide catheter when it is inserted into the lumen of the pusher catheter.

6 Claims, 36 Drawing Sheets

U.S. PATENT DOCUMENTS

| | | | | |
|---|---|---|---|---|
| 2006/0276873 A1* | 12/2006 | Sato | ............................ | 623/1.11 |
| 2007/0005122 A1* | 1/2007 | Inoue | ........................... | 623/1.11 |
| 2007/0270937 A1* | 11/2007 | Leanna | ......................... | 623/1.12 |
| 2008/0051870 A1* | 2/2008 | Kaufmann | .................. | 623/1.11 |
| 2009/0105719 A1* | 4/2009 | Honey et al. | .................. | 606/108 |
| 2010/0063573 A1* | 3/2010 | Hijlkema et al. | ............ | 623/1.11 |
| 2010/0069916 A1* | 3/2010 | Cully et al. | ................... | 606/108 |

FOREIGN PATENT DOCUMENTS

| | | |
|---|---|---|
| JP | 5-220227 | 8/1993 |
| JP | 1-509450 | 8/1999 |
| JP | 2006-51371 | 2/2006 |
| JP | 2006-33423 | 12/2006 |

* cited by examiner

STENT DELIVERY SYSTEM, STENT PLACEMENT METHOD, AND STENT ATTACHMENT METHOD

BACKGROUND OF THE INVENTION

1. Field of the Invention

The present invention relates to a stent delivery system, a stent placement method, and a stent attachment method.

2. Description of Related Art

A procedure known as "drainage" is sometimes performed in the case of bile duct stricture formation. In this procedure, a pusher catheter is used to insert a stent with a through hole into the stricture site, with the stent then retained at this position. A flap is provided at either end of the stent so as to open, thereby reducing movement of the stent following placement.

In order to enable recovery in the case where the inside of the stent becomes occluded over time, part of the stent is pulled out into the small intestine. However, when the stent is positioned in this way, a communication between the small intestine and the bile duct is continually maintained via the stent. As a result, food can flow from the small intestine into the bile duct, and thereby clog the stent. In addition, if coliform bacteria ascend, this can result in formation of a biofilm inside the stent which can cause occlusion.

Stents have been therefore developed in which occlusions are prevented and the stent can be retained for a long period of time by inserting the entirely of the stent into the bile duct. The function of the papilliary sphincter is preserved, preventing the flow of food or coliform bacteria into the stent. In order to facilitate percutaneous endoscopic recovery, this stent has a narrow and long grip piece attached to on the base end portion of the stent which is disposed to the duodenal side, and which is designed to be grasped with forceps or the like.

However, when placing the above-described stent using the conventional stent delivery system, it is necessary pull back the front end of the endoscope from the duodenum toward the stomach in order to expel the grip piece from within the catheter after placement of the stent. During this process, interference can occur between the channel or standing base of the endoscope, and the grip piece, so that there is a risk of catching therebetween.

Further, as shown by the arrow in FIG. 41, the papilla DN disappears from the field of view of endoscope 100 when the endoscope 100 is pulled back toward the stomach. As a result, it becomes difficult to confirm using endoscope 100 whether or not the front end of the grip piece 101 has definitely been expelled out into and positioned within the duodenum. In order to recheck the duodenum via the endoscopic image, the front end of the endoscope 100 must be inserted into the duodenum. Further, this operation becomes even more difficult if the front end of the endoscope 100 has been pulled back into the stomach.

Thus, it is not easy to confirm whether or not the grip piece has been retained at the appropriate position, leading to such problems as an increase in the number of procedure steps and an increase in the duration of the procedure.

The present invention was conceived in view of the above-described circumstances, and has as its objective the provision of a means for enabling the grip piece of the stent to be easily expelled into the duodenum while confirming the duodenal papilla using the endoscope, without having to pull the end of the endoscope from within the duodenum back toward the stomach.

SUMMARY OF THE INVENTION

The stent delivery system according to the first aspect of the present invention is a stent delivery system which is inserted into an endoscope and is for placing a stent inside a body cavity, this stent delivery system being provided with: a long pusher catheter which is flexible; a guide catheter which can pass through the lumen of the pusher catheter in a freely advancing and retracting manner; and a stent which is disposed to the front end of the pusher catheter, and has a cylindrical stent main body into which the guide catheter can be inserted, and a grip piece that is attached so as to extend from the main body and consists of a long narrow member that is pliable and can be disposed in the space between the guide catheter when it is inserted into the lumen of the pusher catheter.

The stent placement method according to the second aspect of the present invention is a method for placing a stent at a specific stent placement site inside a body cavity using the stent delivery system according to the present invention. This stent placement method is provided with a step for inserting the stent delivery system into the body cavity, and guiding the stent to the stent placement site; a step for separating the stent main body and the pusher catheter by pulling the guide catheter toward the base end side; a separating step for separating the stent main body and the pusher catheter while maintaining housing of a portion of the grip piece inside the pusher catheter; and a step for pushing the grip piece outside the pusher catheter after the separating step, by moving the guide catheter toward the front end.

The stent attachment method according to the third aspect of the present invention is provided with a step for inserting the long narrow guide member in between the guide catheter and the pusher catheter, within the lumen of the pusher catheter into which the guide catheter has been inserted; a step for engaging the long narrow grip piece attached to the stent with the guide member which has been pulled out from the front end of the lumen; a step for pulling the guide member toward the base end of the lumen, and pulling the grip piece engaged with the guide member into the lumen; a step for bringing the rear end of the stent and the end surface of the front end of the pusher catheter into contact by pulling the grip piece; and a step for releasing the engagement between the guide member and the grip piece, and pulling the guide member out from the lumen, so that only the grip piece is retained inside the lumen.

DETAILED DESCRIPTION OF THE PREFERRED EMBODIMENTS

Preferred embodiments of the present invention will now be explained with reference to the figures. The same numeric symbol will be applied to compositional elements that are the same in the various embodiments and redundant explanation will be omitted.

First Embodiment

Figure 1:
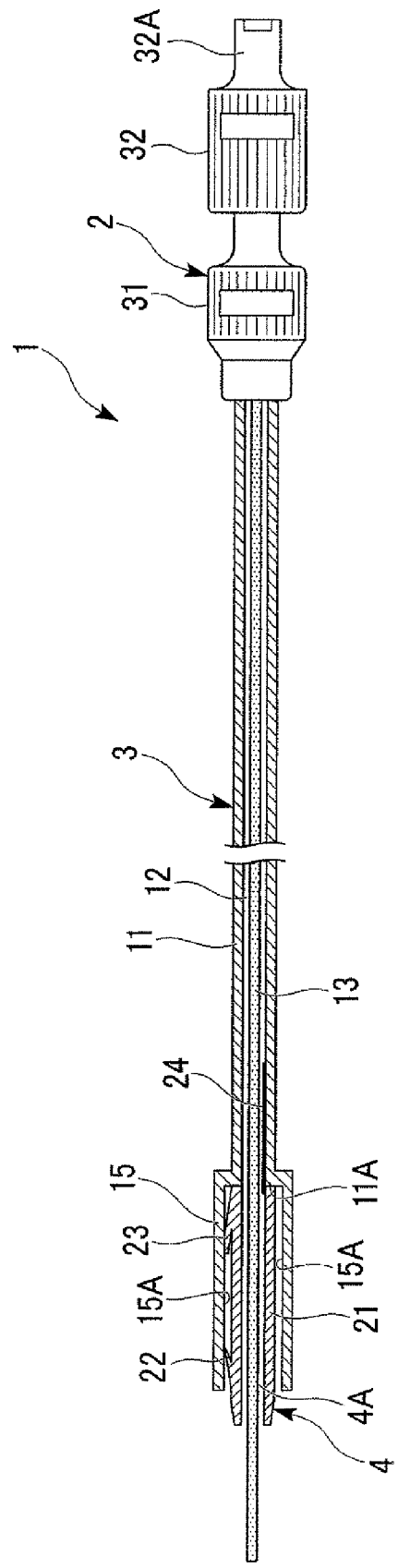
FIG. 1 is a cross-sectional view of the stent delivery system provided with a stent housing in which expands the diameter of the pusher catheter.

As shown in FIG. 1, in the stent delivery system 1, a flexible, long inserted part 3 extends from an operating part 2 which is manipulated by the technician. When the operating part 2 is designated as the base end (hand-held) side, the stent 4 is attached in a freely releasable manner to the front end of the inserted part 3.

The inserted part 3 has a pusher catheter 11. A guide catheter 13 is inserted in a freely advancing and retracting manner into the lumen 12 of the pusher catheter 11. The diameter of the guide catheter 13 is smaller than the diameter of the lumen 12.

A contact surface 11A (front end surface), with which the base end surface of the stent 4 can come into contact, is formed to the front end of the pusher catheter 11, and a stent housing 15 for housing at least a part of the stent 4 is provided in a unitary manner to the front end of the pusher catheter 11. This stent housing 15 is designed by expanding the pusher catheter 11 outward in the radial direction, so that the luminal diameter of the stent housing 15 is larger than the stent diameter. The outer diameter of the stent housing 15 is smaller than the diameter of the operating channel of the endoscope.

Figure 2:
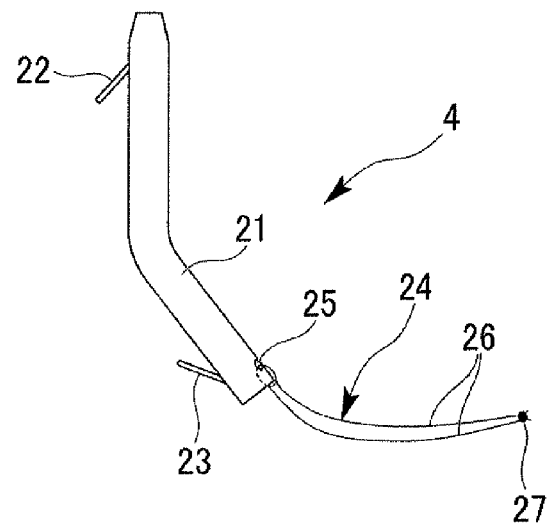
FIG. 2 is a view of the external appearance of the stent.

As shown in FIGS. 1 and 2, stent 4 has a through hole 4A, with respective flaps 22,23 provided to the circular stent main body 21, at either end thereof along the axial direction. A grip piece 24 is attached to the base end of the stent main body 21.

The inner diameter of the stent main body 21 is larger than the guide catheter 13, so that the guide catheter 13 can be inserted therein. The front end of the stent main body 21 is slightly reduced in diameter, and can lightly engage with the guide catheter 13 by means of friction. The outer diameter of the stent main body 21 is smaller than the inner diameter of the stent housing 15, and is larger than the inner diameter of the portion of the pusher catheter 11 that is on the base end side from the stent housing 15. For this reason, the base end surface of the stent 4 can come into contact with a stepped part (contact surface 11A) that forms as a result of the different in the diameters of the pusher catheter 11 and the stent housing 15.

One front end flap 22 is provided, and is formed so as to open naturally toward the base end side. One base end flap 23 is provided, and is formed so as to open naturally toward the front end side. The flaps 22,23 are elastically deformable so as to close under application of external force. Thus, the flaps 22,23 are pushed by the inner wall 15A of the stent housing 15, and fold closed when the stent 4 is housed in the stent housing 15. The length of the stent housing 15 is sufficient to push closed the flaps 22,23 at the front, and so that the front end of the stent 4 is exposed. Note that the number of flaps 22,23 is not limited to that shown in the figures.

The grip piece 24 comprises a loop formed by passing a pliable thread 26 through a hole 25 that is formed in the base end of the stent main body 21. An expanded part 27 is formed by tying thread 26 at a position separated from the stent main body 21. The length of the grip piece 24 is as needed so that it can be pulled out a specific length into the duodenum when the stent 4 is positioned at a stricture site within the bile duct.

The length that the grip piece 24 pulled out into the duodenum is optimally 3-6 cm. However, the optimal length can be selected according to the disease condition. The total length of the grip piece 24 is determined by the length that is pulled out into the duodenum, the total length of the stent, and the location of placement of the stent, but is typically in the range of 3 to 15 cm. The grip piece 24 is housed extending in the axial direction between the inner wall of the pusher catheter 11 and the outer wall of the guide catheter 13. A long thin member formed of polyamide resin for example, may be cited as an example of the thread 26 that forms the grip piece 24. Strength is increased by forming the grip piece 24 into a loop, however, this is not absolutely essential.

The guide catheter 13 is flexible, and has a single lumen formed internally. The guide catheter 13 is longer than the length of the pusher catheter 11 and the stent 4 when these are aligned in the axial direction.

The operating part 2 consists of a first base 31 and a second base 32 that can be attached or released. The base end of the pusher catheter 11 is fixed to the first base 31, and the base end of the guide catheter 13 is fixed to the second base 32. A syringe, not shown in the figures, is attached to a connector 32A that is formed on the base end of the second base 32. A hole is formed inside the second base 32 that communicates from the syringe attached to the connector 32A, to the lumen of the guide catheter 13, enabling supply of a contrast agent. When the two bases 31,32 are connected, the front end of the guide catheter 13 projects out from the front end of the pusher catheter 11 and the stent 4.

Note that when a marker for X-ray imaging is embedded in the front end of the guide catheter 13, then the device can be inserted into bile ducts or other such tubules while viewing the X-ray image.

Next, the method for placing the stent 4 will be explained. The following explanation will discuss a procedure to place the stent 4 at a stricture site which has formed in the bile duct, however, it is also possible to place the stent 4 in other tubules.

First, the endoscope is inserted via a natural orifice such as the patient's mouth, and advanced to the vicinity of the duodenal papilla. The procedure is facilitated by the use of a side view type endoscope that has a lateral field of view.

Figure 3:
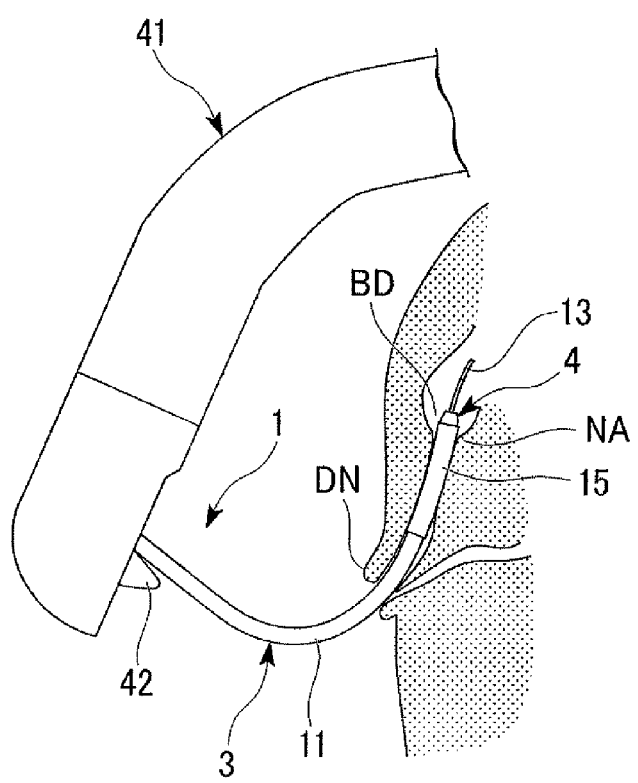
FIG. 3 is a view of the introduction of the device into a stricture site, with the stent housed in the stent housing.

The inserted part 3 of the stent delivery system 1 is inserted into the operating channel of the endoscope, and the stent housing 15 is projected out from the front end of the endoscope. As shown in FIG. 3, a standing base 42 which is provided to the front end of the endoscope 41 is operated to direct the guide catheter 13 and the stent housing 15 toward the papilla DN. The guide catheter 13 and the inserted part 3 are then inserted sequentially via the papilla DN, and stent housing 15 is guided to the stricture site NA that has formed in the bile duct BD. Insertion of the stent delivery system 1 is facilitated if a guide wire (not shown) is employed here.

Figure 4:
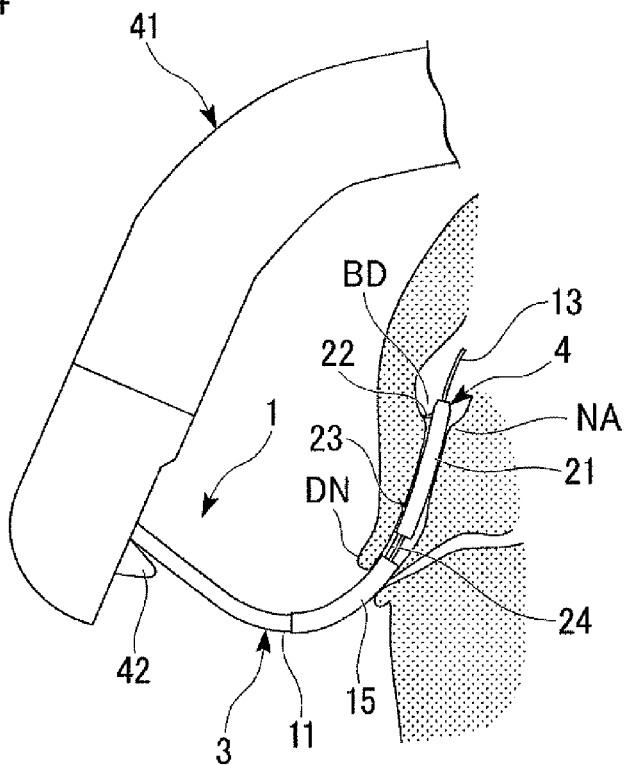
FIG. 4 is a view showing the retraction of the stent housing and the release of the stent.

The base 31 and base 32 are then moved apart, and the base 32 is manipulated to pull stent 4 out from the guide catheter 13. As shown in FIG. 4, by retracting the inserted part 3, the stent housing is lowered and the stent 4 is exposed. Flaps 22,23 which were being pressed down by the stent housing 15 open, and the stricture site NA is positioned between the flaps 22,23. A path for bile flow is thus achieved at the stricture site by means of the conduit in the stent main body 21, and movement of the stent 4 is checked by the flaps 22,23.

Figure 5:
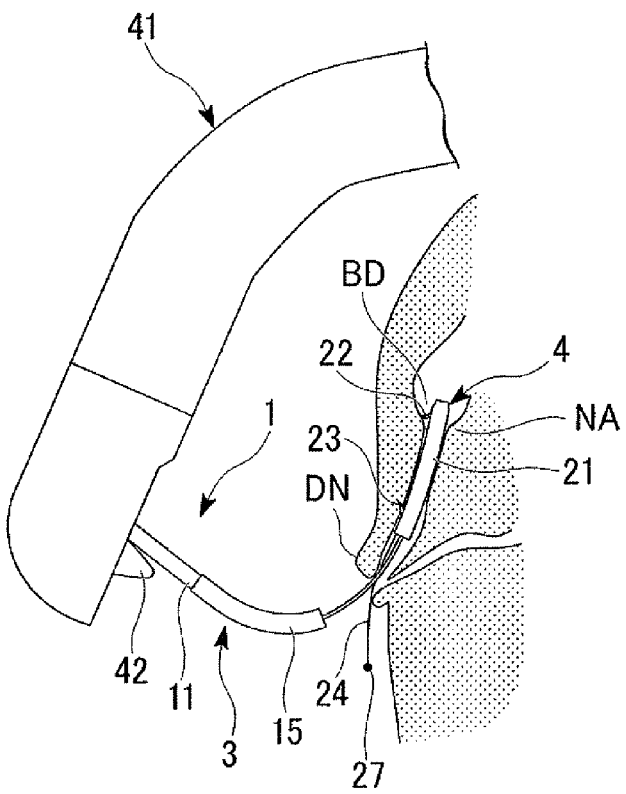
FIG. 5 is a view showing the pusher catheter pulled out from the bile duct, and the grip piece pulled out into the duodenum.

As shown in FIG. 5, during the process of pulling out the pusher catheter 11 from the bile duct BD, the grip piece 24 is exposed along the bile duct BD and is pulled out around 3-6 cm from the papilla DN into the duodenum. When subsequently recovering stent 4, the grip piece 24 is gripped with a forceps or snare that is passed through the endoscope 41. The grip piece 24 can be easily gripped due to the presence of the expanded part 27, and the stent 4 can then be easily pulled out from the bile duct BD by pulling the grip piece 24.

In this embodiment, a stent housing 15 which has a larger inner diameter than the outer diameter of the stent main body 21 is provided at the front end of the pusher catheter 11. As a result, the stent 4 can be introduced into the stricture site NA with the flaps 22,23 in the closed state. In the conventional art, the flap on the base end side of the stent is curved toward the front end, so that the base end flap bends during insertion into the papilla and the flap cannot fully function. However, in this embodiment, bending of the flaps 22,23 is prevented, so that the stent 4 can be placed with certainty.

Second Embodiment

Figure 6:
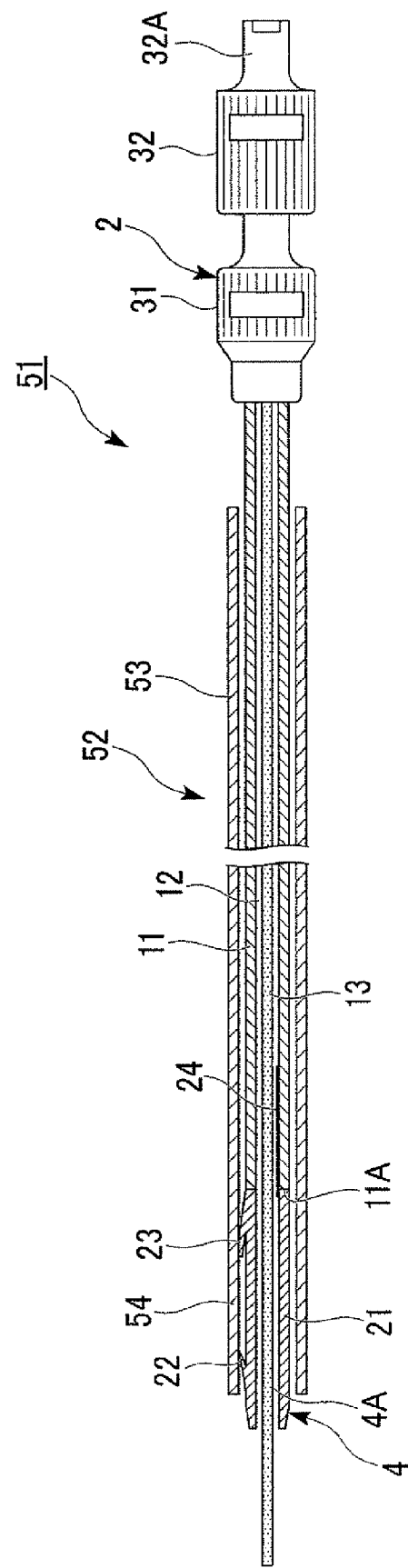
FIG. 6 is a cross-sectional view of the stent delivery system in which an outer sheath is provided as the stent housing.

As shown in FIG. 6, the design of the inserted part 52 in this stent delivery system 51 differs from that of the first embodiment.

In this inserted part 52, a flexible outer sheath 53 is provided in a freely sliding manner on the outside of the pusher catheter 11. The pusher catheter 11 has a diameter that is roughly constant up to its tip, and the contact surface 11A at its front end comes into contact with the base end of the stent main body 21. The outer sheath 53 has a roughly constant diameter. When the base of this outer sheath 53 is positioned so that there is a fixed distance maintained between it and the operating part 2, the front end surface of the outer sheath 53 projects out beyond the pusher catheter 11 toward the front end. The front end part of the outer sheath 53 forms a stent housing 54 for housing stent 4. The length of the stent housing 54 is adjusted so that the portion of the stent housing 54 that is toward the front end side beyond the flaps 22,23 of stent 4 is exposed when the stent 4 is in contact with the pusher catheter 11. The inner diameter of the outer sheath 53 is larger than that of the stent main body 21, but smaller than the outer diameter when the flaps 22,23 are open. As a result, the stent 4 is housed with the flaps 22,23 in a closed state. Note that the guide catheter 13 extends farther forward than the outer sheath 53 and the stent 4.

The method for placing the stent 4 will be explained next.

Figure 7:
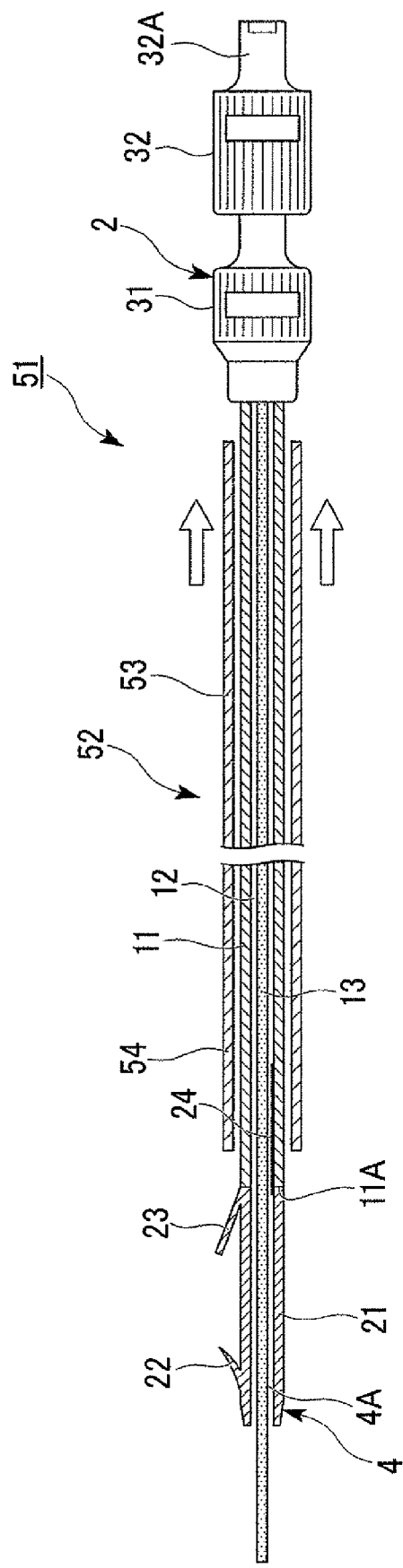
FIG. 7 is a view in which the outer sheath has been retracted, causing the flaps of the stent to open.

The inserted part 52 of the stent delivery system 51 is passed though the endoscope 41, and the pusher catheter 11 and the outer sheath 53 are introduced in unison into the bile duct BD via the papilla DN. Once stent 4 has been guided to the stricture site NA, the pusher catheter 11 is stopped and the outer sheath 53 is retracted. As shown in FIG. 7, the flaps 22,23 of the stent 4 open, positioning the stent 4 at the stricture site NA. The base 31 and the base 32 are moved apart, and the base 32 is manipulated to pull the guide catheter 13 from the stent 4, Next, the pusher catheter 11 and the outer sheath 53 are pulled back, and the grip piece 24 is passed from the bile duct BD through the papilla DN, and pulled out into the duodenum.

In this embodiment, by providing a slidable outer sheath 53 to the outside of the stent 4 and the pusher catheter 11, it is possible to prevent bending at the contact wall 11A between the pusher catheter 11 and the stent 4, thereby positioning the stent 4 with certainty. By fixing the position of the pusher catheter 11 and pulling the outer sheath 53 toward the handheld side, it is possible to position stent 4. As a result, it is possible to release the stent 4 at the desired position.

Third Embodiment

Figure 8:
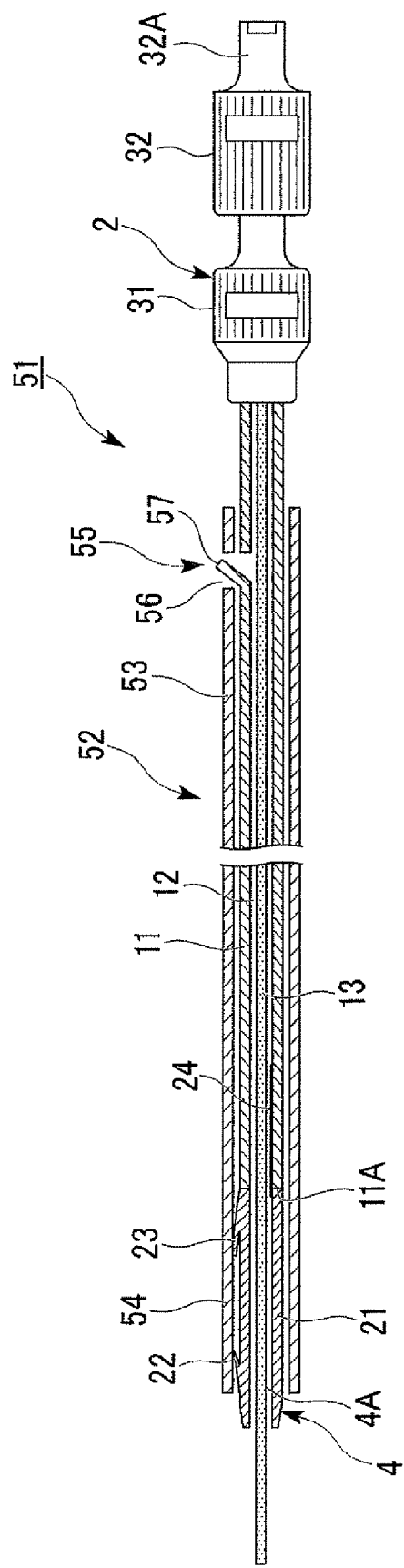
FIG. 8 is a view showing the structure of the restricting member.

As shown in FIG. 8, in this stent delivery system 51, a restricting member 55 for limiting the movement of the outer sheath 53 with respect to the pusher catheter 11 is provided to the inserted part 52.

The restricting member 55 consists of a hole 56 that is provided at the base end side of the outer sheath 53 to the portion that is pulled and turned from the endoscope to the outside of the body; and a claw 57 that is formed to the pusher catheter 11 at a location corresponding to the position where the hole 56 is formed.

The claw 57 is formed by introducing a cutout to the pusher catheter 11 and elevating it from the base end forward. The size of the claw 57 is such that it can insert into the hole 56 and pass through the outer sheath 53.

Figure 9:
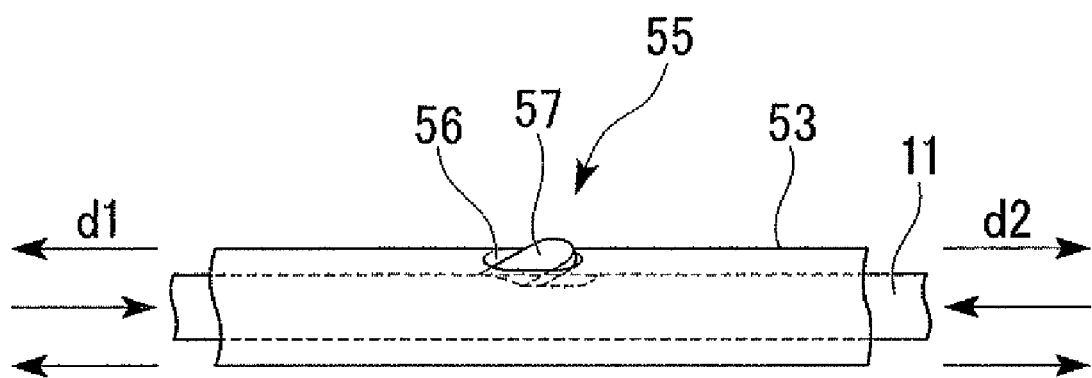
FIG. 9 is a view for explaining the operation of the restricting member.

The claw 57 is inclined so as to open with its front end side employed as the starting point for opening. As a result, when the claw 57 passes through the hole 56 and catches on the outer sheath 53, the claw 57 is caught and serves as a stopper in the case of movement in the direction of relative advance, or pushing in, of outer sheath 53, as shown by the arrow d1 in FIG. 9. In contrast, the engagement of the claw 57 is released, allowing easy sliding, in the case of movement in the direction of relative retraction, or withdrawal, of the outer sheath 53, as shown by the arrow d2 in FIG. 9.

When placing the stent 4, the inserted part 52 is passed through the endoscope 41 and inserted into the papilla DN. Once the stricture site NA is reached, the position of the pusher catheter 11 is fixed in place and only the outer sheath 53 is retracted. Since restricting member 55 does not function in this direction, the outer sheath 53 is retracted relative to the pusher catheter 11 and the stent 4 is released.

In this embodiment, the situation in which only the outer sheath 53 is pushed in with respect to the restricting member 55 does not occur. As a result, it is possible to place the stent 4 at the desired location with certainty while preventing folding over of the flaps 22,23.

Fourth Embodiment

Figure 10:
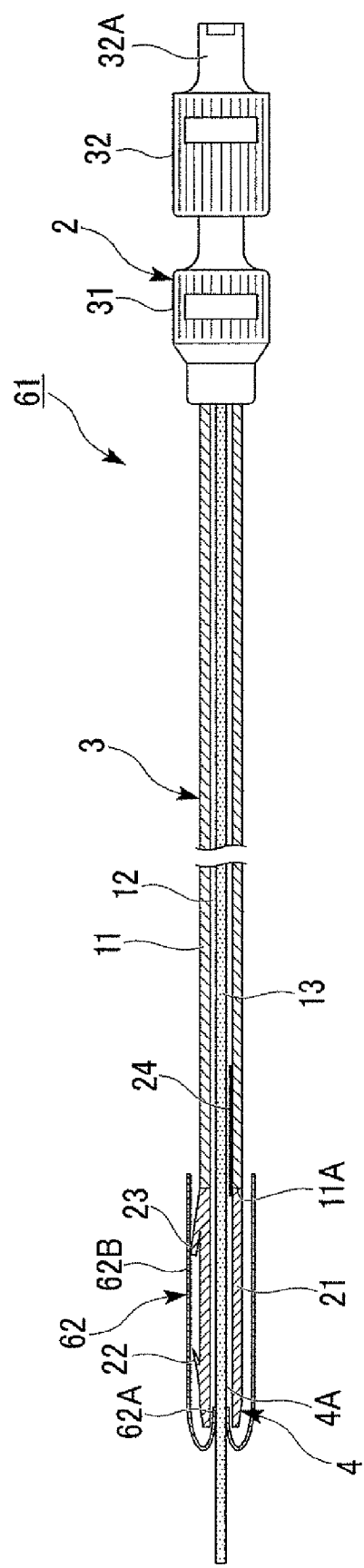
FIG. 10 is a cross-sectional view of the stent delivery system in which a cover catheter is provided as the stent housing.
Figure 11:
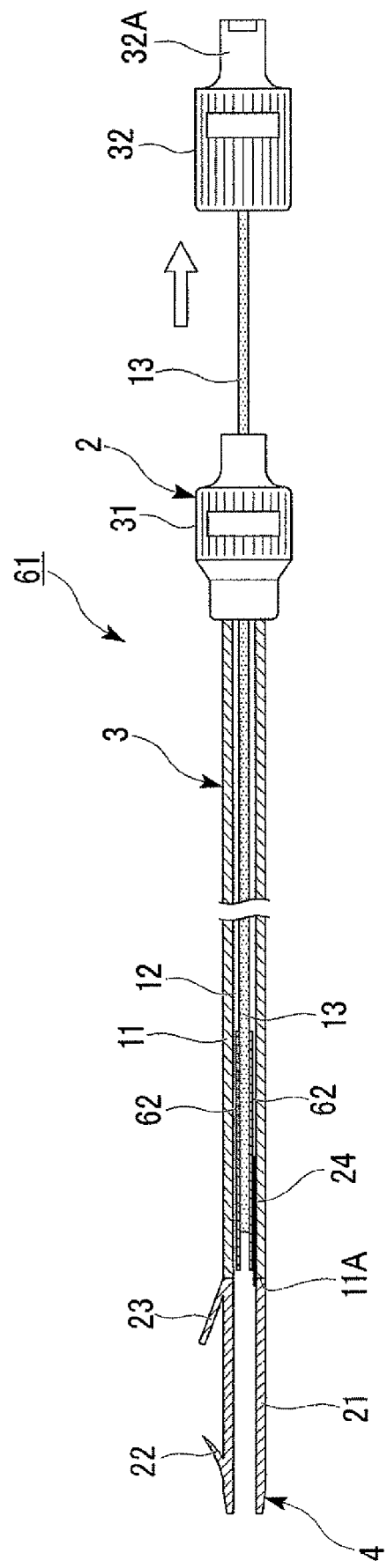
FIG. 11 is a view in which the cover catheter has been pulled back, causing the flaps to open.

As shown in FIG. 10, this stent delivery system 61 is provided with a cover catheter 62.

The cover catheter 62 consists of a tubular member that is connected to the front end of the guide catheter 13 via adhesion, etc.

When attaching the stent 4, the cover catheter 62 is extended forward beyond its connection 62A with the guide catheter 13. The cover catheter 62 has a constricted diameter along the guide catheter 13, so that the guide catheter 13 and the cover catheter 62 can pass through the through hole 4A of the stent 4. When the stent 4 is in contact with the contact surface 11A of the pusher catheter 11, which has a roughly constant outer diameter, the cover catheter 62 folds over and covers the stent 4. When the amount of insertion of the guide catheter 13 is adjusted in advance so that its connection 62A with the cover catheter 62 is disposed inside the through hole 4A of the stent 4, the cover catheter 62 is pulled out from within the stent main body 21, folds back near the front end of the stent main body 21, and returns toward the base end side, passing over the area of contact between the stent 4 and the pusher catheter 11. The diameter of the cover catheter 62 when in this folded back state is larger than the stent main body 21, but smaller than the outer diameter of the stent main body 21 when the flaps 22,23 are spread wide. As a result, the flaps 22,23 are pushed by the cover catheter 62 and close. The cover catheter 62 thus has the two functions: housing the flaps 22,23 and fixing the stent 4 in place.

When placing the stent 4, the inserted part 3 is passed through the endoscope 41 with the stent 4 is covered by the cover catheter 62. The inserted part 3 is then passed through the papilla DN and guided to the stricture site NA in the bile duct BD. The inserted part 3 can be inserted smoothly into the bile duct BD since the flaps 22,23 are covered by the cover catheter 62 and do not become caught on the papilla DN.

The guide catheter 13 is retracted when the second base 32 is pulled with respect to the first base 31, and the cover catheter 62, which is linked to the guide catheter 13 via connection 62A is also pulled toward the base end side. In other words, part 62B, which is disposed to the outer periphery of the stent 4 is also pulled. The part 62B which is disposed to the outer periphery is pulled along the outer periphery of the stent 4 toward the front end side, and then is pulled into the through hole 4A of stent 4. As shown in FIG. 1, the cover catheter 62 is pulled entirely within the pusher catheter 11, along with the guide catheter 13, thus exposing the stent 4, and allowing the flaps 22,23 to open. When the pusher catheter 11 is retracted, the stent 4 is released into position.

In this embodiment, the stent 4 is covered by the cover catheter 62, thus preventing folding and bending of the flaps 22,23. Further, insertion from the papilla DN into the bile duct BD can be carried out smoothly. Since an outer sheath (such as the outer sheath 53 in FIG. 6) to cover roughly the entire length of the pusher catheter 11 is not necessary, passage through the endoscope 41 is facilitated and operability improves.

Fifth Embodiment

This embodiment relates to a method for attaching the stent 4 and a design for disposing the grip piece 24 without loosening inside the pusher catheter 11.

Figure 12:
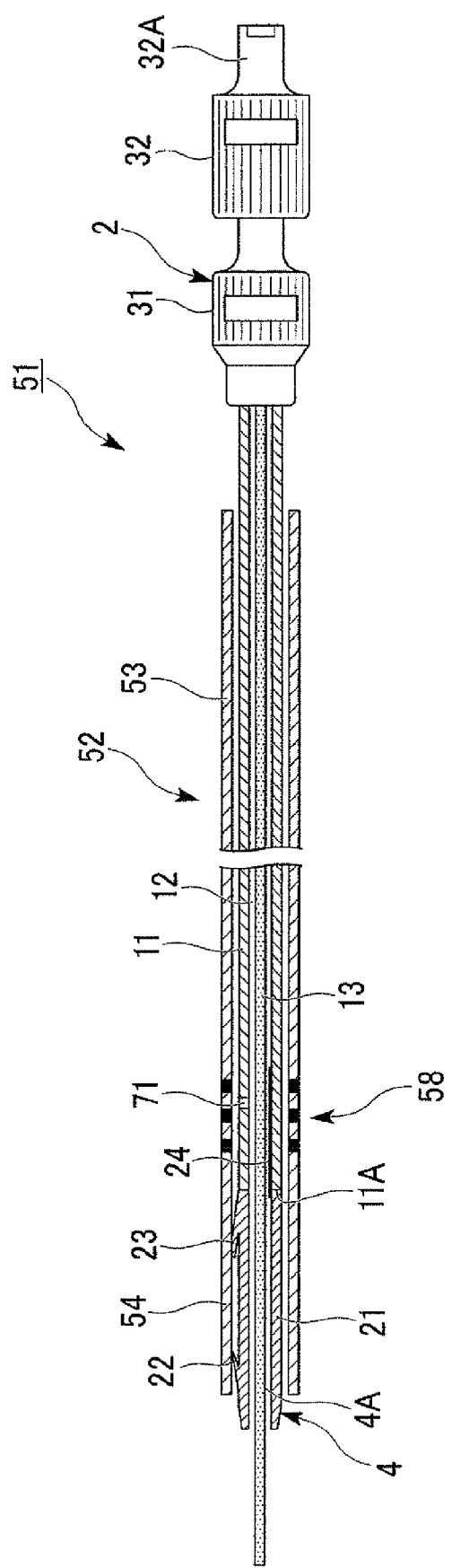
FIG. 12 is a cross-sectional view showing the structure which enables the grip piece to be easily disposed.

As shown in FIG. 12, the pusher catheter 11 is provided with one lateral hole 71 at a position that is a fixed length from the contact surface 11A at the front end. The position of formation of this lateral hole 71 is approximately equal to the length of the grip piece 24, or is farther toward the base end side. Note that the grip piece 24 forms a looped shape in which a thread 26 is attached to the stent main body 21. In addition, pusher markings 58 which serve as standards for positioning the grip piece 24 are provided to the outer sheath 53. The pusher markings 58 are provided farther toward the front than the base end of the grip piece 24 when the stent 4 is attached, and at a position that is within a specific distance, 1 centimeter for example, from the base end of the grip piece 24. The pusher markings 58 are provided with a color or pattern that can be confirmed via the endoscopic image.

When placing the stent 4 using this stent delivery system 51, the pusher catheter 11 is inserted until the pusher markings 58 are roughly aligned with the papilla DN. The position of the pusher catheter 11 is fixed in place and the outer sheath 53 is retracted, allowing the flaps 22,23 of the stent 4 to open. The guide catheter 13 is then retracted. The guide catheter 13 is pulled inside the pusher catheter 11, releasing the stent 4. The outer sheath 53, the pusher catheter 11 and the guide catheter 13 are then pulled out from the papilla DN, and the grip piece 24 is expelled. The end of the grip piece 24 extends toward the base end side beyond the pusher marking 58, so that it is expelled into the duodenum with certainty.

Next, the method for attaching the stent 4 using the stent delivery system 51 will be explained.

Figure 13:
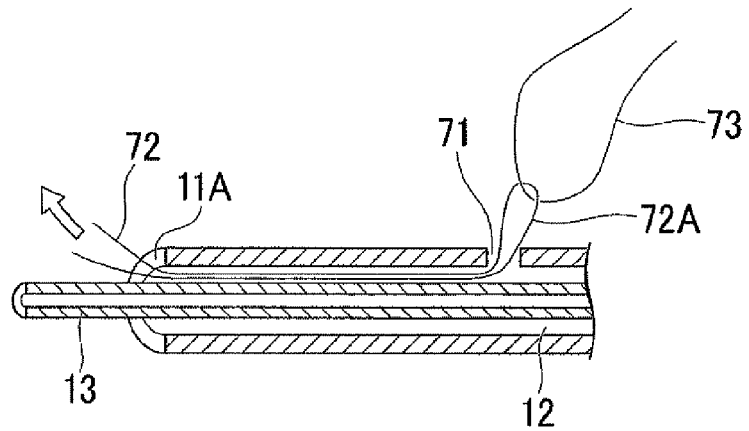
FIG. 13 is a view in which a wire has been passed through prior to attachment of the stent.

As shown in FIG. 13, with the guide catheter 13 passed into the pusher catheter 11, a wire 72, which is the first guide member, is inserted from the front end side into the lumen 12 of the pusher catheter 11. The wire 72 is bent in the middle to form a rough U-shape, and the bent part 72A is inserted into the lumen 12 first. The bent part 72A is projected out from the lateral hole 71 toward the outer periphery of the pusher catheter 11. A lower thread 73, which is the second guide member, is passed through this bent part 72A.

The lower thread 73 employs a material that is twice as long as the distance from the contact surface 11A of the pusher catheter 11 to the lateral hole 71, and the approximate middle portion of the lower thread 73 passed through the wire 72.

Figure 14:
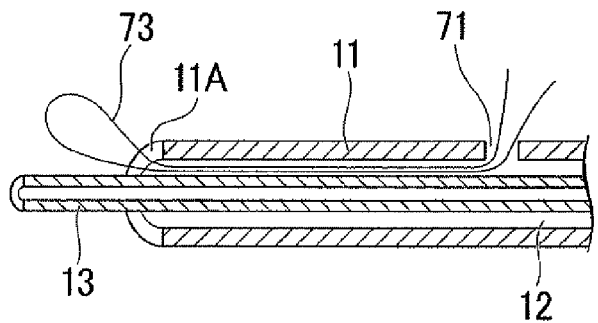
FIG. 14 is a view in which the lower thread has been passed using the wire.

When the wire 72 is pulled back, the lower thread 73 which is engaged via the bent part 72A is pulled into the lumen 12 via the lateral hole 71. When the wire 72 is pulled out from the contact surface 11A side, then, as shown in FIG. 14, the lower thread 73 passes from the lateral hole 71 to the contact surface 11A, and is pulled into a looped shape.

Figure 15:
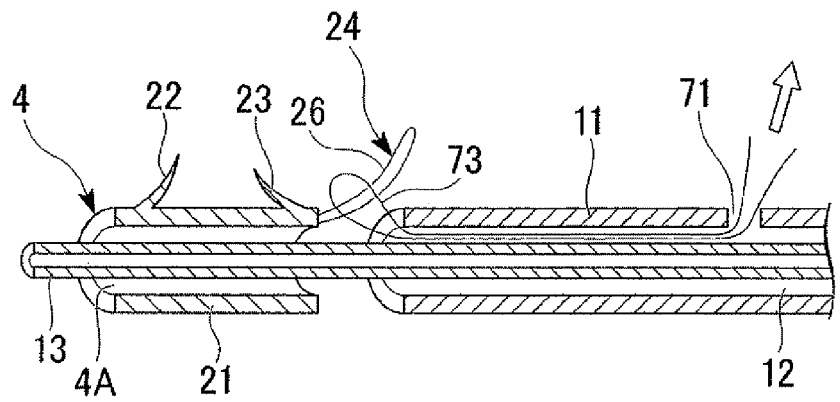
FIG. 15 is a view in which the lower thread has been caught on the grip piece.

As shown in FIG. 15, the grip piece 24 of the stent 4 is passed through the looped part of the lower thread 73. Lower thread 73 is pulled back, pulling the grip piece 24 which is engaged with lower thread 73, into the lumen 12. The grip piece 24 is pulled, without loosening, in between the pusher catheter 11 and the guide catheter 13, and the lower thread 73 is pulled out from the grip piece 24 and the pusher catheter 11 by pulling one end thereof. As shown in FIG. 12, the grip piece 24 is thus disposed along approximately the axial line in between the lumen 12 of the pusher catheter 11 and the guide catheter 13.

Placement of the stent 4 is carried out in the same manner as in the second embodiment. The grip piece 24 is disposed in between the pusher catheter 11 and the guide catheter 13 without loosing, thus improving the sliding properties of the guide catheter 13. In addition, the grip piece 24 does not become caught on the endoscope 41 or the standing base, so that the grip piece 24 can be expelled with certainty. This thus resolves the problem encountered in conventional stents in which expelling of the grip piece is uncertain.

Figure 16:
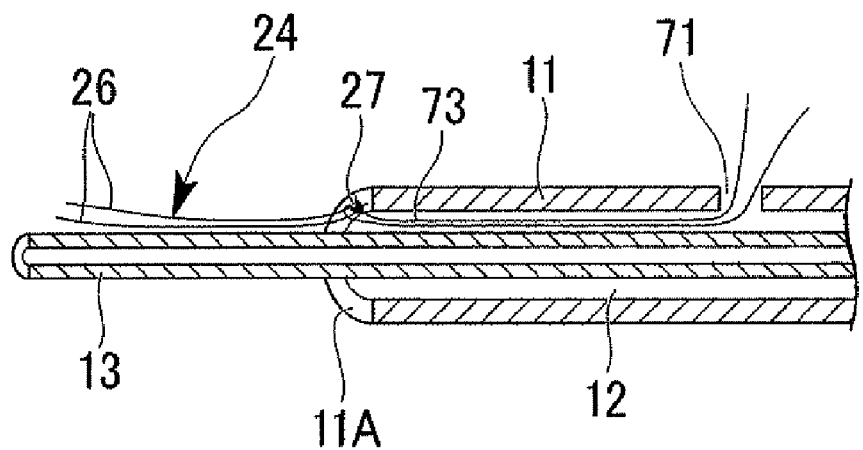
FIG. 16 is a view for explaining the attachment method when an expanded part is provided to the grip piece.
Figure 17:
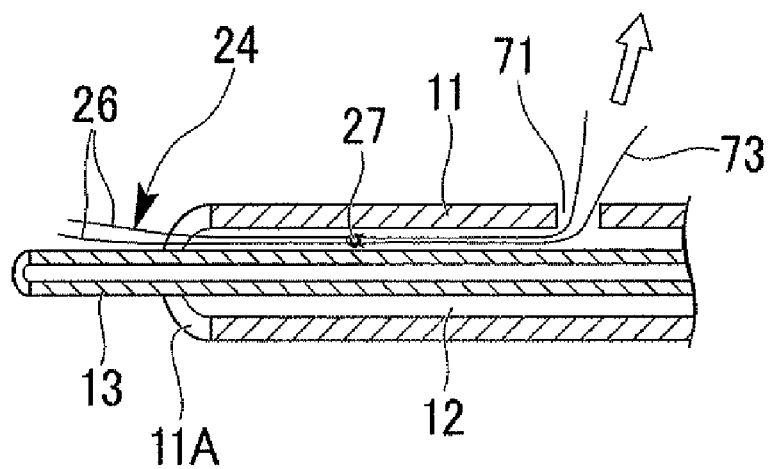
FIG. 17 is a view in which the grip piece has been disposed inside the lumen using the lower thread.

As shown in FIG. 16, if an expanded part 27 is provided to the grip piece 24 here, then the lower thread 73 can be caught on this expanded part 27. As shown in FIG. 17, the grip piece 24 which includes an expanded part 27 is housed so as to extend in the axial direction in between the pusher catheter 11 and the guide catheter 13. The grip piece 24 is of a size to permit its housing in between the pusher catheter 11 and the guide catheter 13. By providing an expanded part 27 in this way, the operation of attaching the stent 4 is facilitated. As disclosed previously, gripping during recovery is made easier due to the presence of this expanded part 27.

Note that the grip piece 24 need not be a loop, but rather may be a single thread 26, or have a design in which an expanded part 27 is provided to a single thread 26. The lateral hole 71 may be provided farther toward the base end side than the length of the grip piece 24. It is also acceptable to employ an opening in the base end surface of the pusher catheter 11, without providing a lateral hole 71.

The stent 4 can be frictionally engaged with the pusher catheter 11 so that it does not fall off even if an outer sheath 53 is not provided. The means for preventing bending and folding of the flaps 22,23 of the stent 4 during insertion is not limited to the outer sheath 53. Rather, other designs according to other embodiments are also acceptable. Note that a first guide member (wire 72) and a second guide member (lower thread 73) are used in this embodiment, however, an assembly of the same design is also possible using only a lower thread 73.

Sixth Embodiment

This embodiment relates to a method for placing the stent 4, and, specifically, to the method for expelling the grip piece 24.

Figure 18:
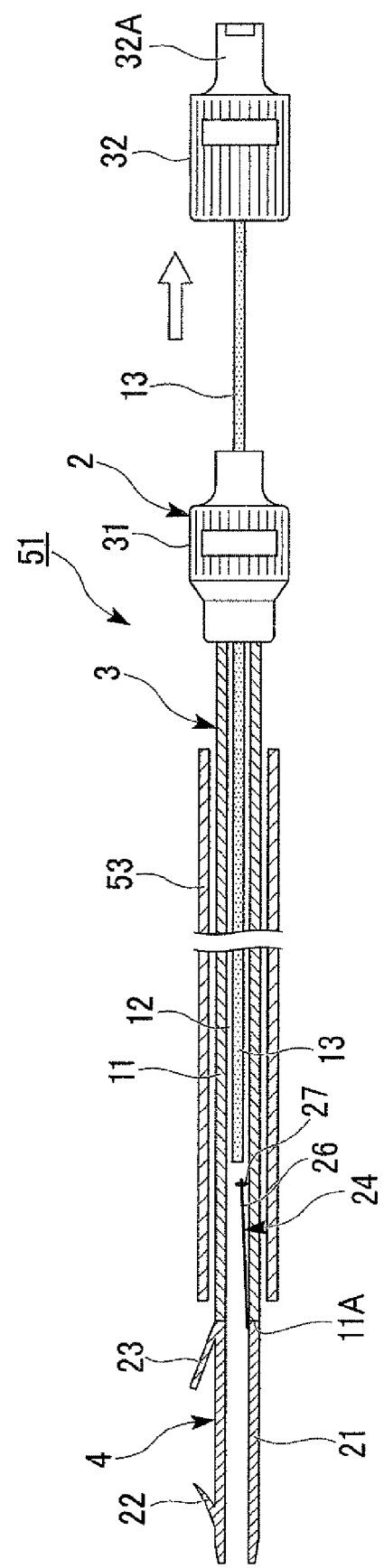
FIG. 18 is a view for explaining the method for expelling the grip piece.

When expelling the grip piece 24 after placing the stent 4 at the stricture site NA, the second base 32 of the operating part 2 is pulled, thereby pulling the guide catheter 13 toward the base end side from the grip piece 24, as shown in FIG. 18. The guide catheter 13 is retracted, and the grip piece 24 is disposed inside the space within the empty lumen 12.

Figure 19:
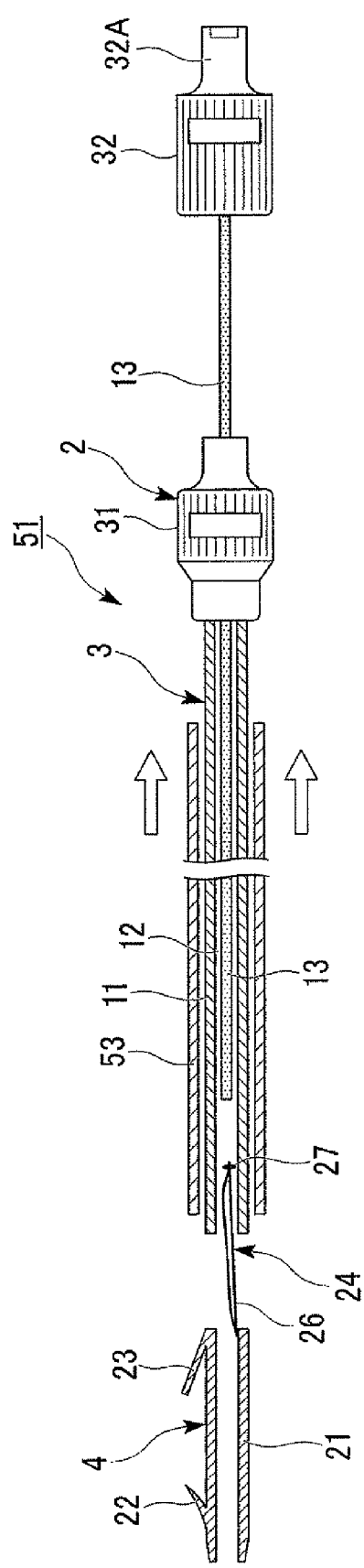
FIG. 19 is a view in which the stent has been released.

As shown in FIG. 19, the front end of the pusher catheter 11 is pulled back to a position where it is within the duodenum and can be visualized with the endoscope. The amount that the pusher catheter 11 is pulled back at this time is less than the length of the grip piece 24 in the axial direction. The pusher catheter 11 is pulled away from the main body 21 of the stent 4, and the grip piece 24 is pulled out into the duodenum, passing from the bile duct BD into the papilla DN. However, part of the grip piece 24 remains inside the pusher catheter 11 at this stage.

Figure 20:
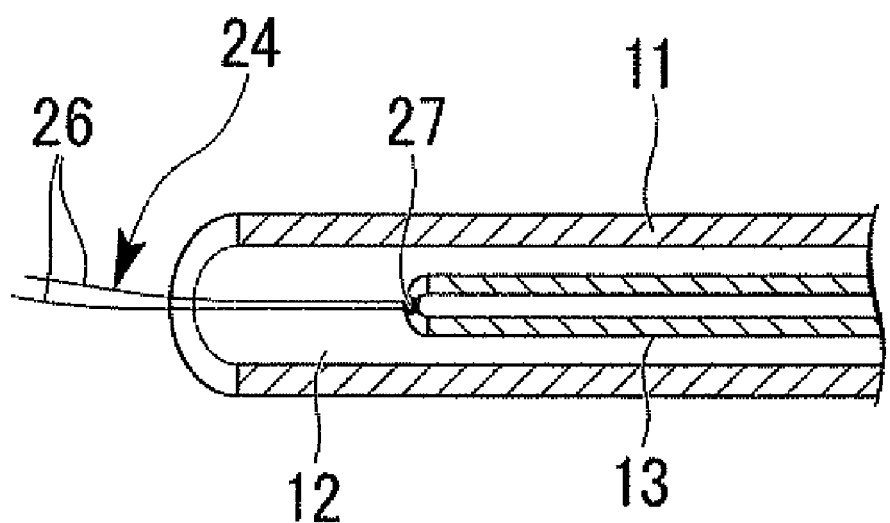
FIG. 20 is a view in which the expanded part of the grip piece is pushed out using the guide catheter.
Figure 21:
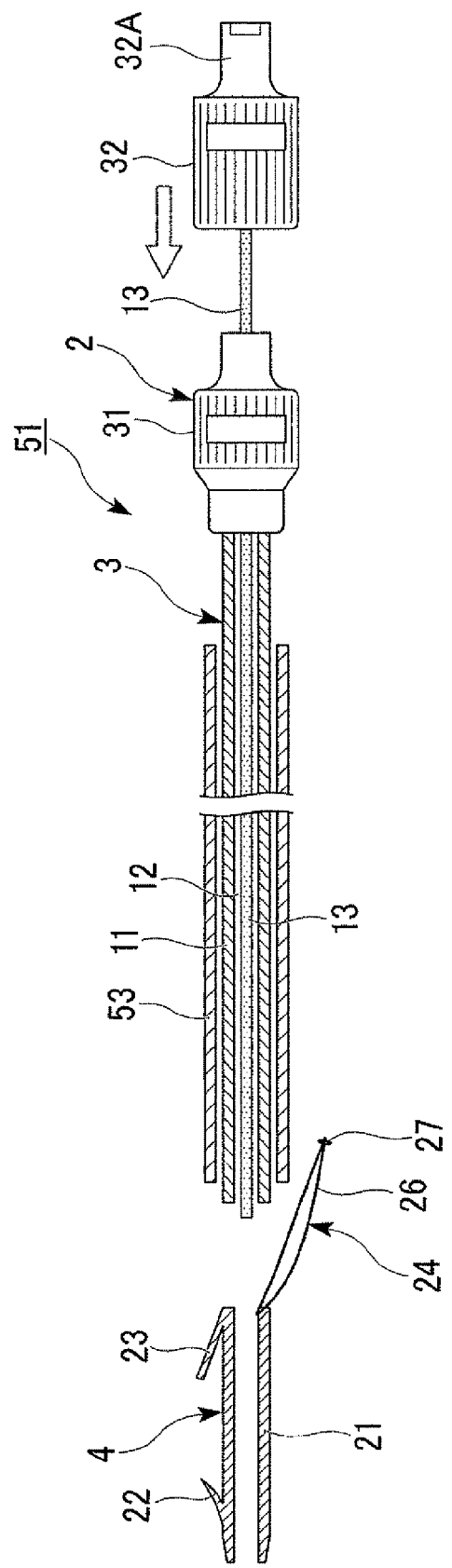
FIG. 21 is a view in which the grip piece has been pushed out.

The second base 32 is again pushed in to advance the guide catheter 13, causing the front end surface of the guide catheter 13 to come into contact with the expanded part 27, and push the grip piece 24 toward the front end, as shown in FIG. 20. As shown in FIG. 21, when the front end of the guide catheter 13 is projected out from the pusher catheter 11, the grip piece 24 is completely expelled to the outside of the pusher catheter 11, inside the duodenum in this case.

Figure 22A:
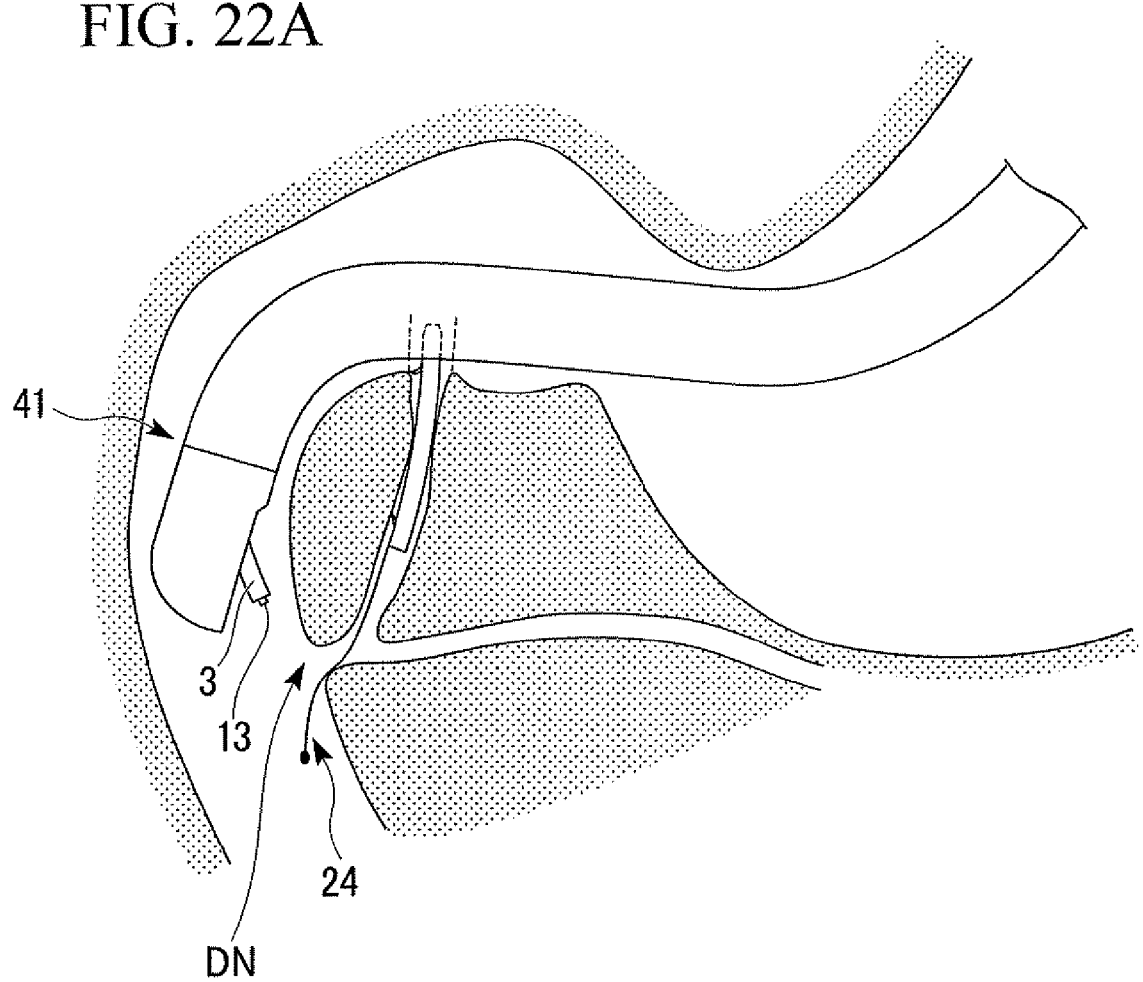
FIG. 22A is a view showing the position of the endoscope when the grip piece is pushed out.
Figure 22B:
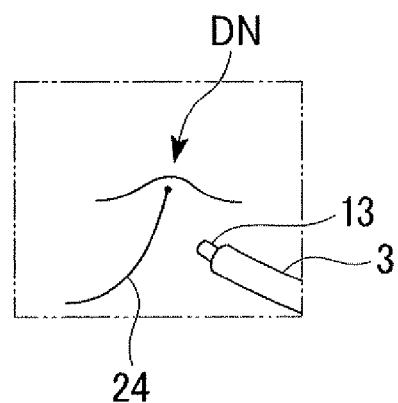
FIG. 22B is a view showing the line of view of the endoscope in the arrangement shown in FIG. 22A.

It is not necessary to pull the endoscope 41 back toward the stomach in order to expel the grip piece 24 here. As a result, as shown in FIGS. 22A and 22B, the grip piece 24 can be expelled by moving the guide catheter 13 forward while maintaining the papilla DN in the field of view of the endoscope 41.

In this method for placing the stent 4, it is possible to reduce the amount of movement of the pusher catheter as compared to the case where the grip piece is expelled by retracting the pusher catheter a distance which is greater than the length of the grip piece. In the conventional art, the distance between the endoscope and the papilla is short, so that the grip piece cannot be expelled if the pusher catheter is not pulled into the endoscope. The grip piece may become caught on the standing base of the endoscope in this case. In this embodiment, the grip piece is expelled from the lumen 12 of the pusher catheter 11 into the duodenum, so there is no interference with the standing base 42, nor does the grip piece 24 become caught on the standing base 42.

Note that if the endoscope is pulled along with the pusher catheter, it does not become caught on the standing base, however the insertion and extraction of the endoscope increases the stress on the patient. In this embodiment, the grip piece 24 is pushed out using the guide catheter 13, 50 that expulsion of the guide piece is carried out smoothly and with certainty.

An expanded part 27 is provided to the grip piece 24, thus facilitating pushing out of the grip piece 24 with the guide catheter 13. Even if an expanded part is not provided, however, the grip piece 24 can be easily expelled in this placement method.

Seventh Embodiment

This embodiment relates to a method for placing the stent 4, and particularly to a method for expelling the grip piece 24 and to the appropriate design therefor.

Figure 23:
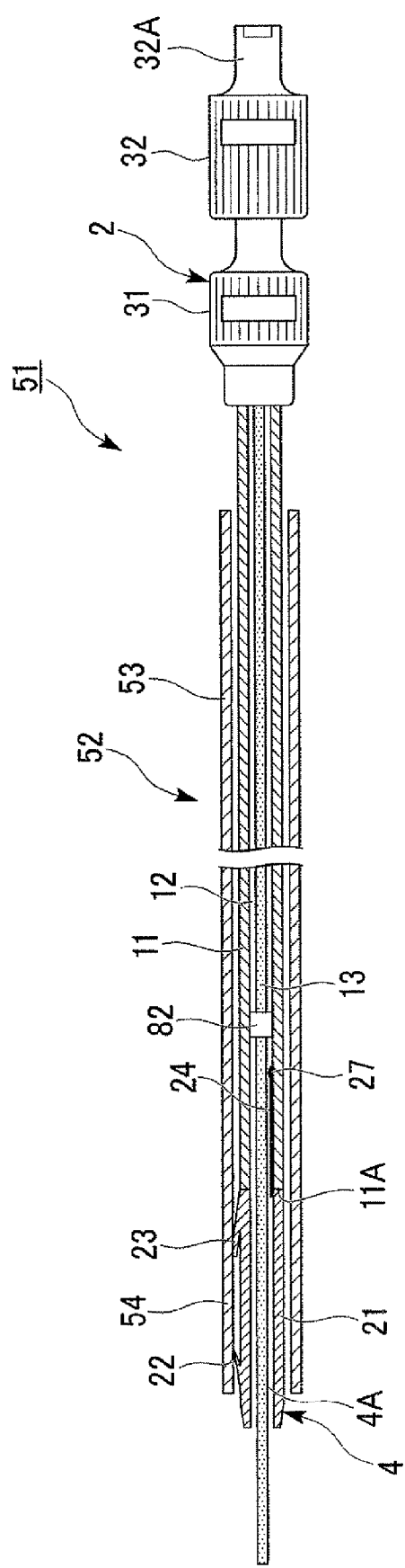
FIG. 23 is a view in which a pusher for pushing out the grip piece has been provided to the guide wire.

As shown in FIG. 23, a pusher 82 is provided to the guide catheter 13 in this stent delivery system 51. The pusher 82 is disposed to the front end of the guide catheter 13, closer to the hand-held side than the grip piece 24. This pusher 82 increases the outer diameter of the guide catheter 13. The outer diameter of the pusher 82 is equal to or less than the diameter of the lumen 12, and has a roughly cylindrical shape which is larger than the outer diameter of the guide catheter 13.

Figure 24:
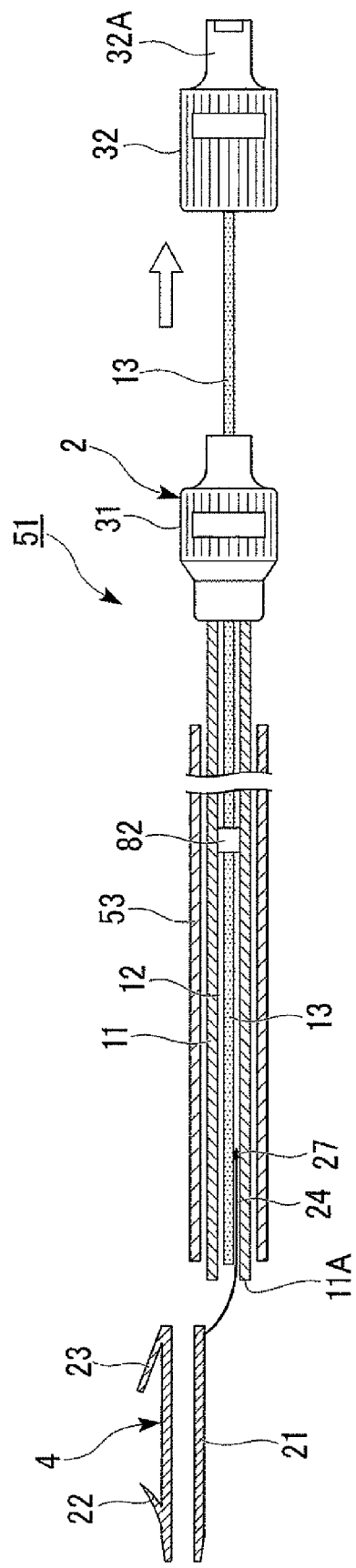
FIG. 24 is a view in which the stent has been released.

When placing the stent 4, the stent 4 is guided to the stricture site NA in the bile duct BD. The outer sheath 53 is retracted, allowing the flaps 22,23 of the stent 4 to open. When the guide catheter 13 is retracted and pulled inside the pusher catheter 11 is shown in FIG. 24, the stent 4 and the guide catheter 13 are disengaged and the stent 4 is released. The guide catheter 13 does not need to be pulled back beyond the end of the grip piece 24, nor is it necessary for the guide catheter 13 to be pulled back when it is not engaged with the stent 4.

A portion of the grip piece 24 is pulled out from the papilla DN when the pusher catheter 11 is pulled back from the papilla DN into the duodenum. The amount that the pusher catheter 11 is pulled back at this time is less than the length of the grip piece 24 in the axial direction. A portion of the grip piece 24 remains inside the pusher catheter 11 at this stage.

Figure 25:
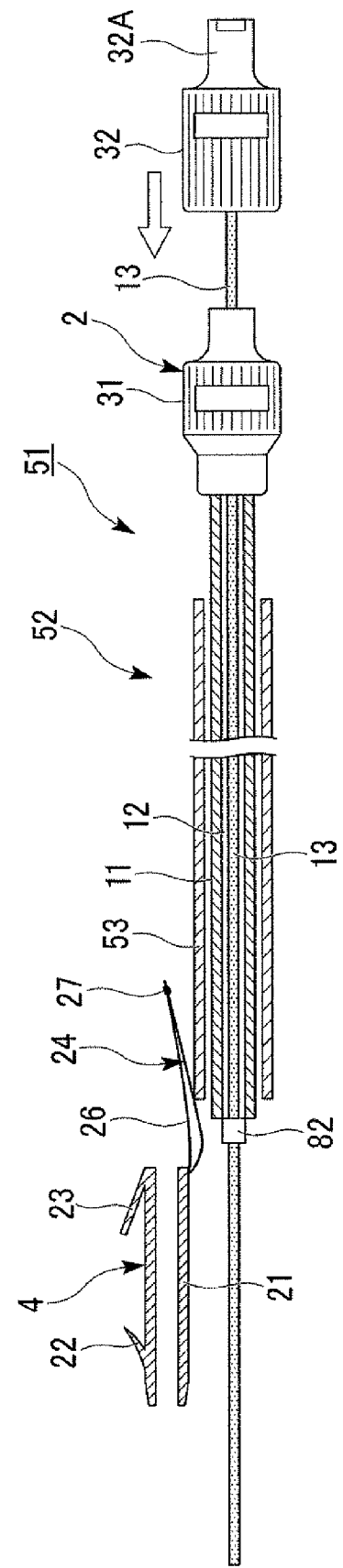
FIG. 25 is a view in which the grip piece has been pushed out by the pusher.

As shown in FIG. 25, when the guide catheter 13 is pushed in, the pusher 82 moves forward in unison with the guide catheter 13, and the pusher 82, where the outer diameter of the guide catheter 13 is increased, comes into contact with the expanded part 27, pushing the grip piece 24 toward the front end. As a result, the grip piece 24 is expelled from the pusher catheter 11.

This stent delivery system 51 enables the grip piece 24 to be disposed inside the duodenum with certainty. By providing a pusher 82, the expelling of the grip piece 24 can be carried out smoothly and with certainty. The amount of manipulation of the guide catheter 13 can be decreased. Pushing with the pusher 82 is facilitated by providing an expanded part 27 to the grip piece 24, however, a design which does not include this expanded part 27 is also acceptable.

Figure 26:
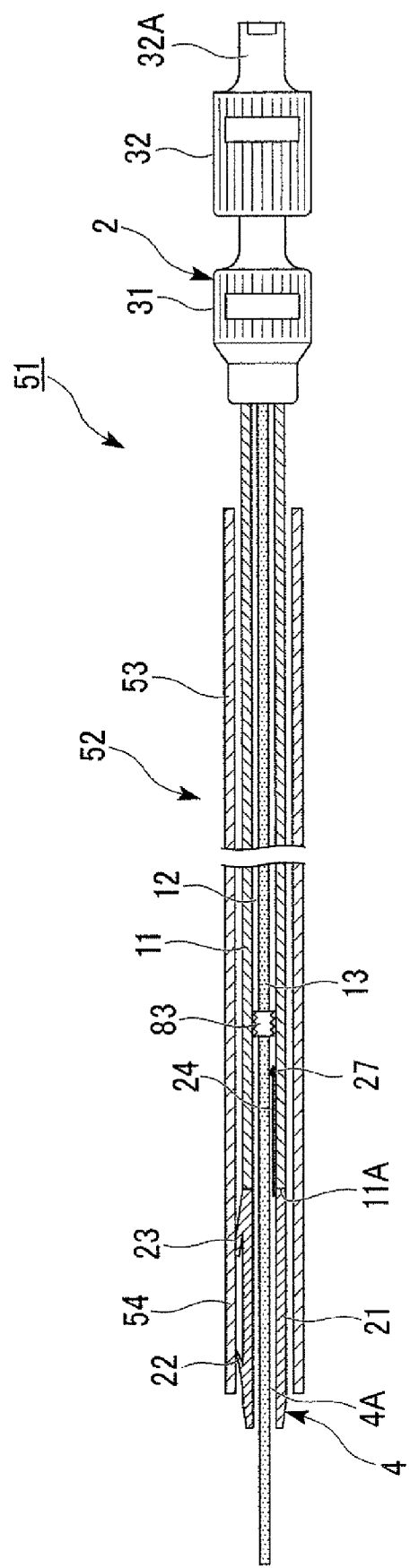
FIG. 26 is a view in which a brush is provided as the pusher.
Figure 27:
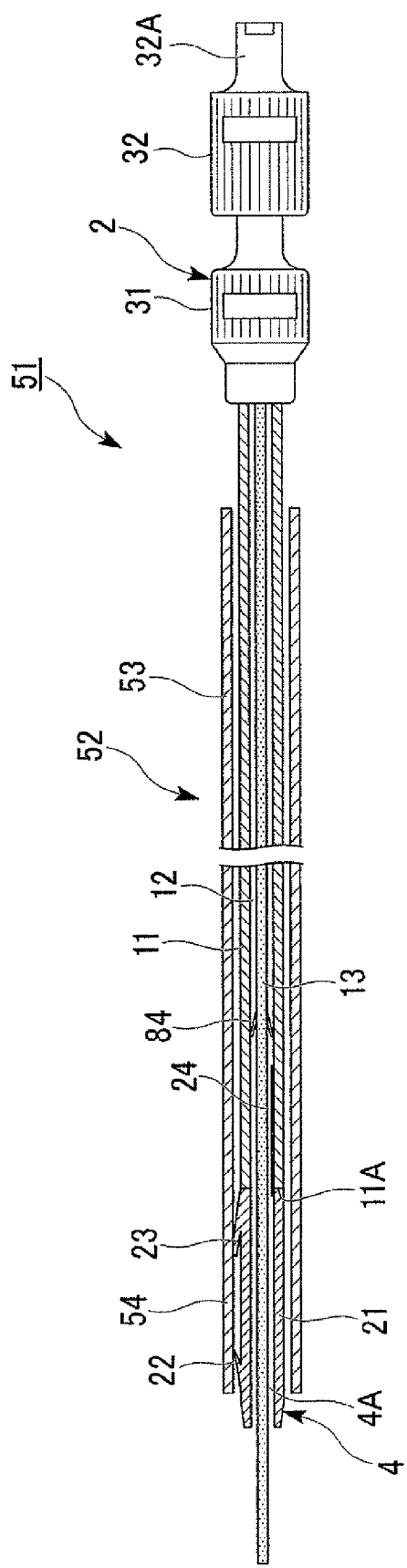
FIG. 27 is a view in which a cut out is provided as the pusher.

Here, as shown in FIG. 26, a brush 83 that is provided to the front end of the guide catheter 13 closer to the hand-held side than the end of the grip piece 24 may be employed as the pusher. Further, as shown in FIG. 27, it is also acceptable to employ a cut-out 84 provided to the front end of the guide catheter 13 closer to the hand-held side than the end of the grip piece 24 as the pusher. This cut-out 84 is formed by introducing a cut-out to the outer circumference of the guide catheter 13 from the front end, and elevating this cut-out in the radial direction outward. It is preferable to provide a plurality of cut-outs 84 so that the grip piece 24 can be pushed out with surety. In the case of these brush 83 or cut-out 84 type pushers as well, these parts are formed such that they increase the outer diameter of the guide catheter 13 at this portion. As a result, a brush 83 or cut-out 84 type pusher achieves the same effects as those of the pusher 82.

Eighth Embodiment

Figure 28:
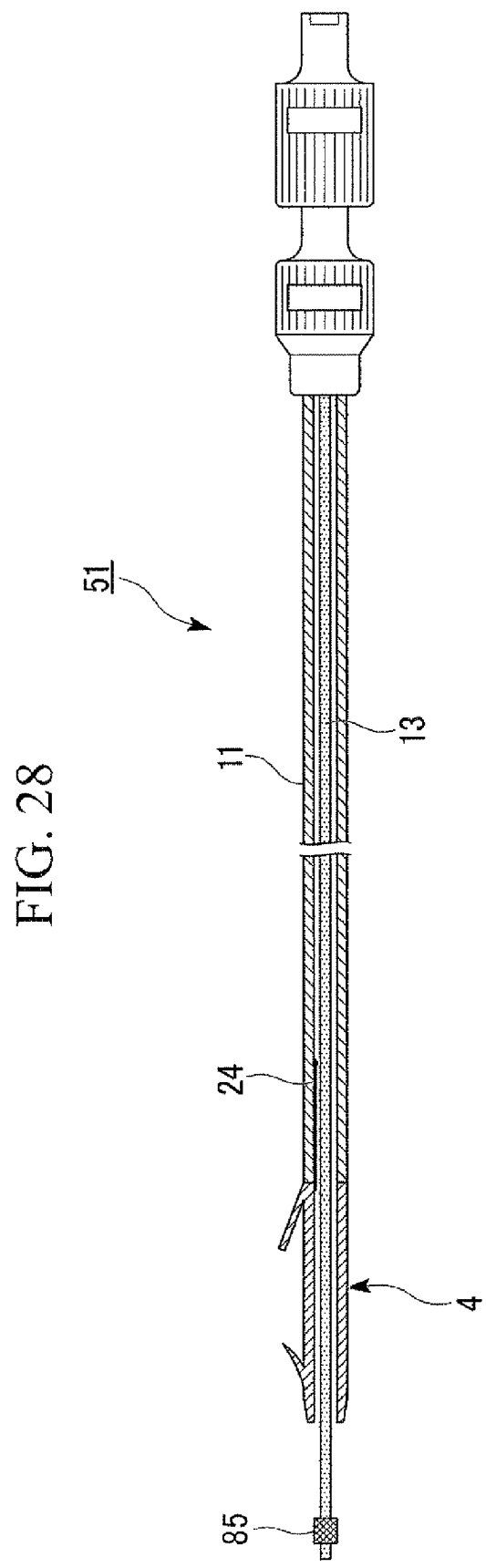
FIG. 28 is a view showing an example in which the pusher is formed of a material which can contract.

In the stent delivery system 51 shown in FIG. 28, the pusher 58 is a material which can contract in the radial direction, such as, for example, urethane, polystyrene or the like which have foaming and contracting properties.

Figure 29:
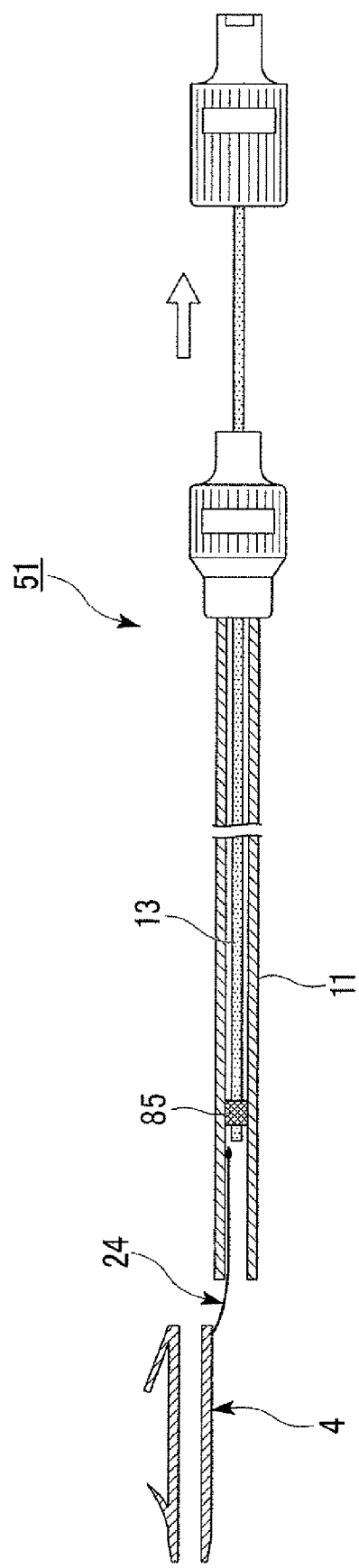
FIG. 29 is a view in which the stent has been released.

In this stent delivery system 51, the pusher 85 deforms when the engagement between the stent 4 and the guide catheter 13 is released by pulling the guide catheter 13 toward the hand-held side, as shown in FIG. 29.

Figure 30:
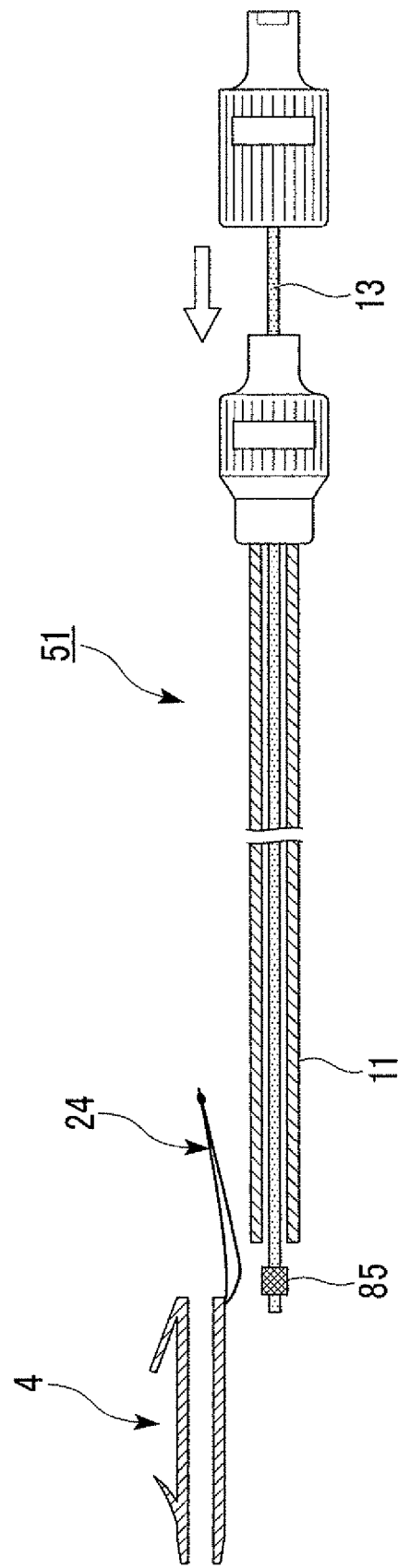
FIG. 30 is a view in which the grip piece has been pushed out by the pusher.

As a result, there is no interference with the grip piece 24 and the pusher 85 can be moved closer to the hand-held side than the grip piece 24. Next, as shown in FIG. 30, the guide catheter 13 is reinserted, causing the grip piece 24 to be pushed by the pusher 85, and thereby be expelled from inside of the pusher catheter 11.

In this stent delivery system 51, the pusher 85 does not need to be constantly positioned closer to the hand-held side than the end of the grip piece 24 when the pusher 85 is inside the pusher catheter 11. As a result, it becomes possible to provide the pusher 85 farther toward the front end side of the guide catheter 13, thus reducing the amount that the guide catheter 13 must be projected out from the pusher catheter 11 when reinserting the guide catheter 13 in order to expel the grip piece 24. As a result, it becomes even easier to operate the device.

Ninth Embodiment

Figure 31:
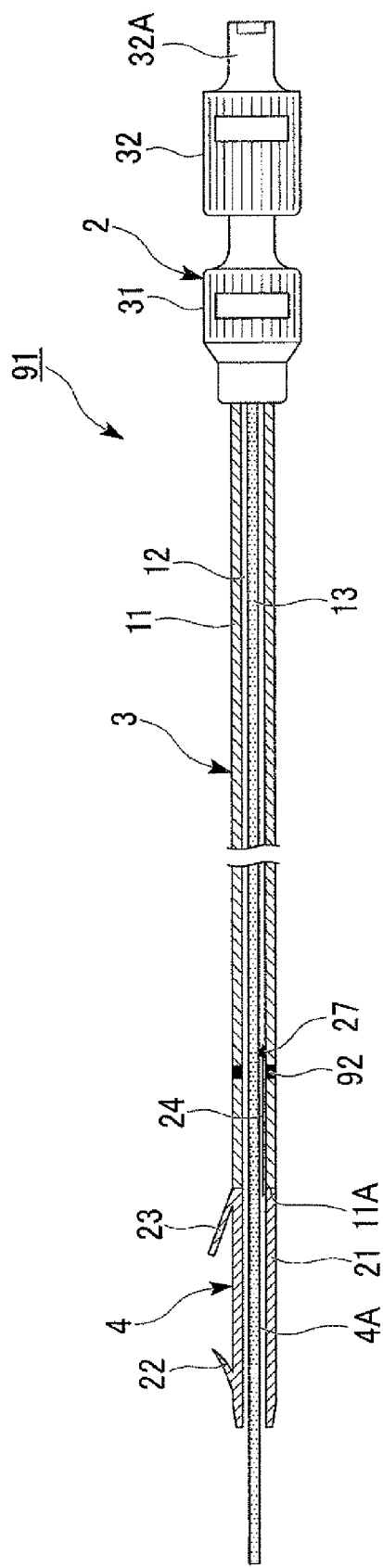
FIG. 31 is a view in which a pusher marking is provided to the front end side of the pusher catheter.

As shown in FIG. 31, a pusher marking 92 which consists of an indicator on the outer periphery of the front end side of the pusher catheter 11 is provided in this stent delivery system 91. The pusher marking 92 is provided near the base end of the grip piece 24, to a position farther toward the front end than the base end of the grip piece 24 when the stent 4 is attached. The pusher marking 92 consists of a color or pattern that can be recognized in the endoscopic image.

Figure 32:
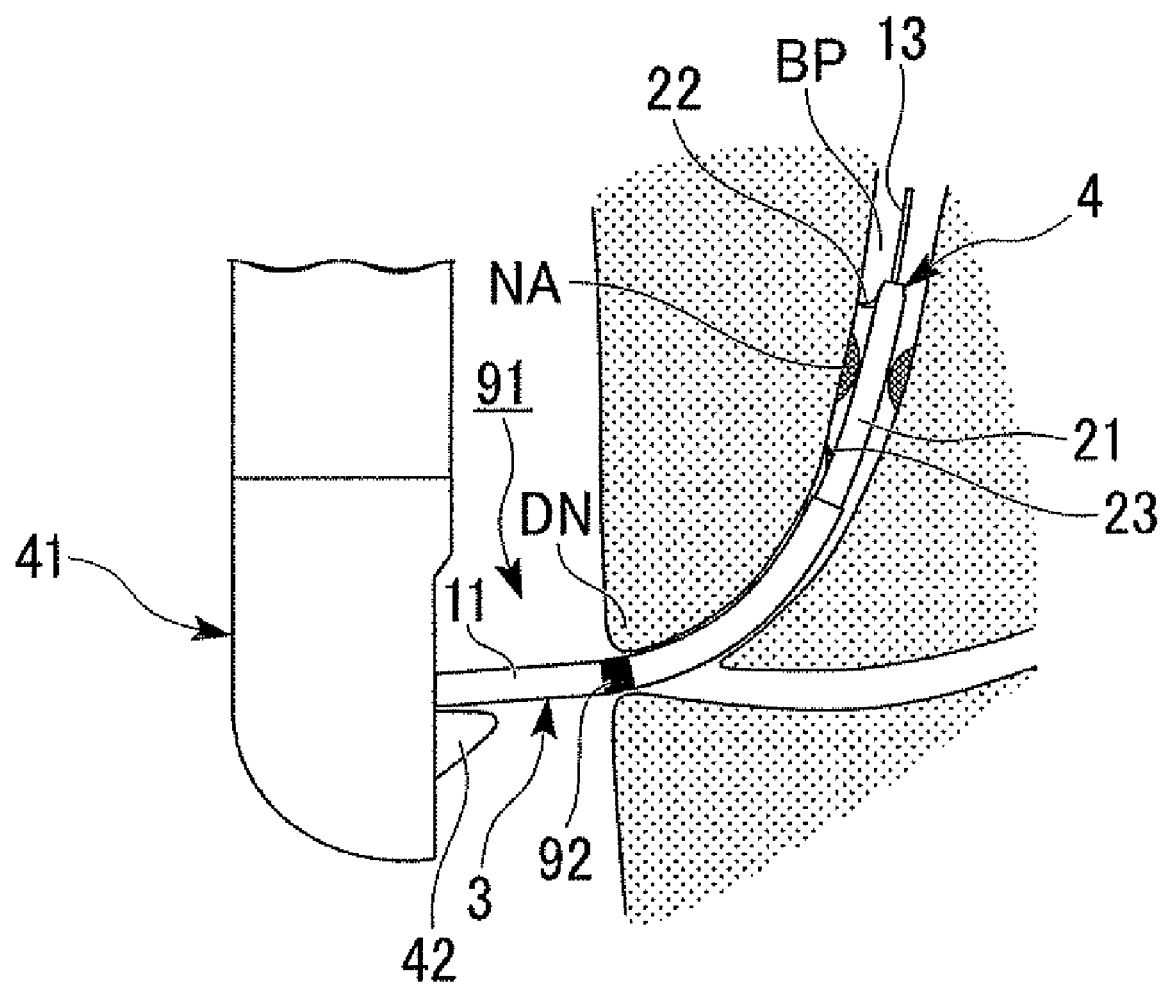
FIG. 32 is a view for explaining the extent of insertion when the pusher marking is aligned with the papilla.

As shown in FIG. 32, when placing the stent 4, the pusher catheter 11 is inserted until the pusher marking 92 roughly aligns with the papilla DN. The position of the pusher catheter 11 is fixed in place, and the guide catheter 13 is retracted. The guide catheter 13 is then pulled into the pusher catheter 11, releasing the stent 4. The pusher catheter 11 and the guide catheter 13 are then pulled out from the papilla DN, expelling the grip piece 24. The end of the grip piece 24 originally extends to the base end side beyond the pusher marking 92, so that the grip piece 24 can be expelled into the duodenum with certainty.

It is not possible to directly visualize the position of the stent 4 inside the bile duct BD using the endoscopic image. However, if the pusher marking 92 is aligned with the papilla DN, then it is possible to position the stent 4 within limits that allow the grip piece 24 to be expelled into the duodenum. Thus, the grip piece 24 can be disposed with certainty using the endoscopic image, facilitating subsequent recovery of the stent 4. The length for expelling the grip piece 24 into the duodenum is approximately 3 to 6 cm. Accordingly, the pusher marking 92 is preferably positioned 3 to 6 cm forward from the base end of the grip piece 24.

Note that pushers 82-84 may be suitably employed to expel the grip piece 24. In addition, if a stent housing such as outer sheath 53 or the like is employed, folding and bending of the flaps 22, 23 can be prevented. In addition, when the pusher catheter 11 is formed of a transparent material, a marking may be provided to the guide catheter 13. When employing the outer sheath 53, it may be made of a material that permits confirmation of the pusher marking 92. Alternatively, a marking may be provided to the outer sheath 53.

Figure 33:
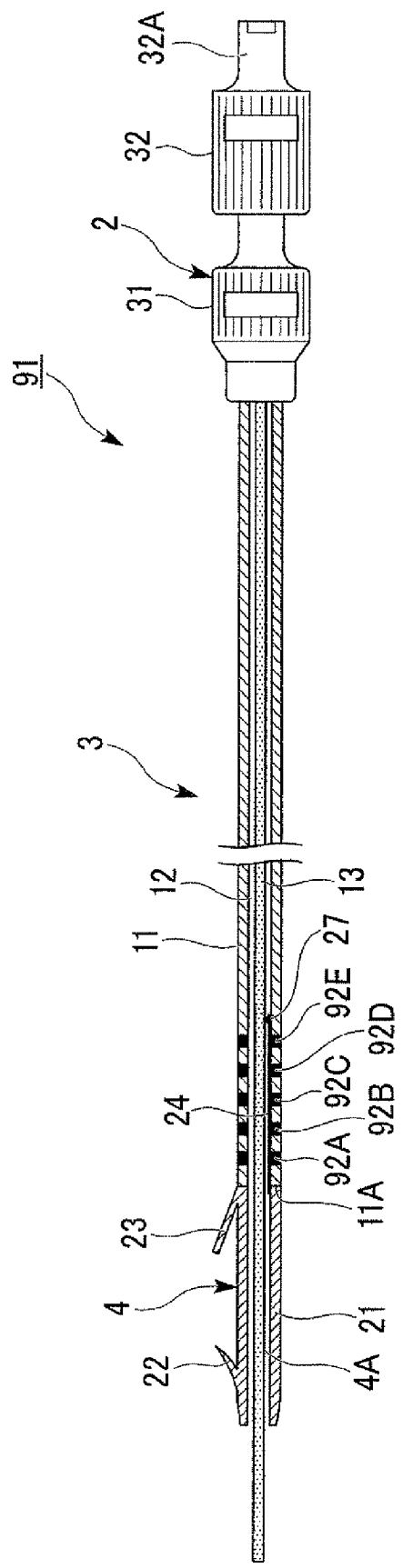
FIG. 33 is a view in which multiple length measurement markings are provided to the pusher catheter.

Here, as shown in FIG. 33, a plurality of length measurement markings 92A-92E may be provided in the axial direction of the pusher catheter 11 as indicators. The grip piece 24 of the stent 4 extends farther toward the base end side than the length measurement marking 92E, which is the length measurement marking that is closest to the base end side. All of the length measurement markings 92A-92E have a color or pattern which can be confirmed via the endoscopic image.

Figure 34:
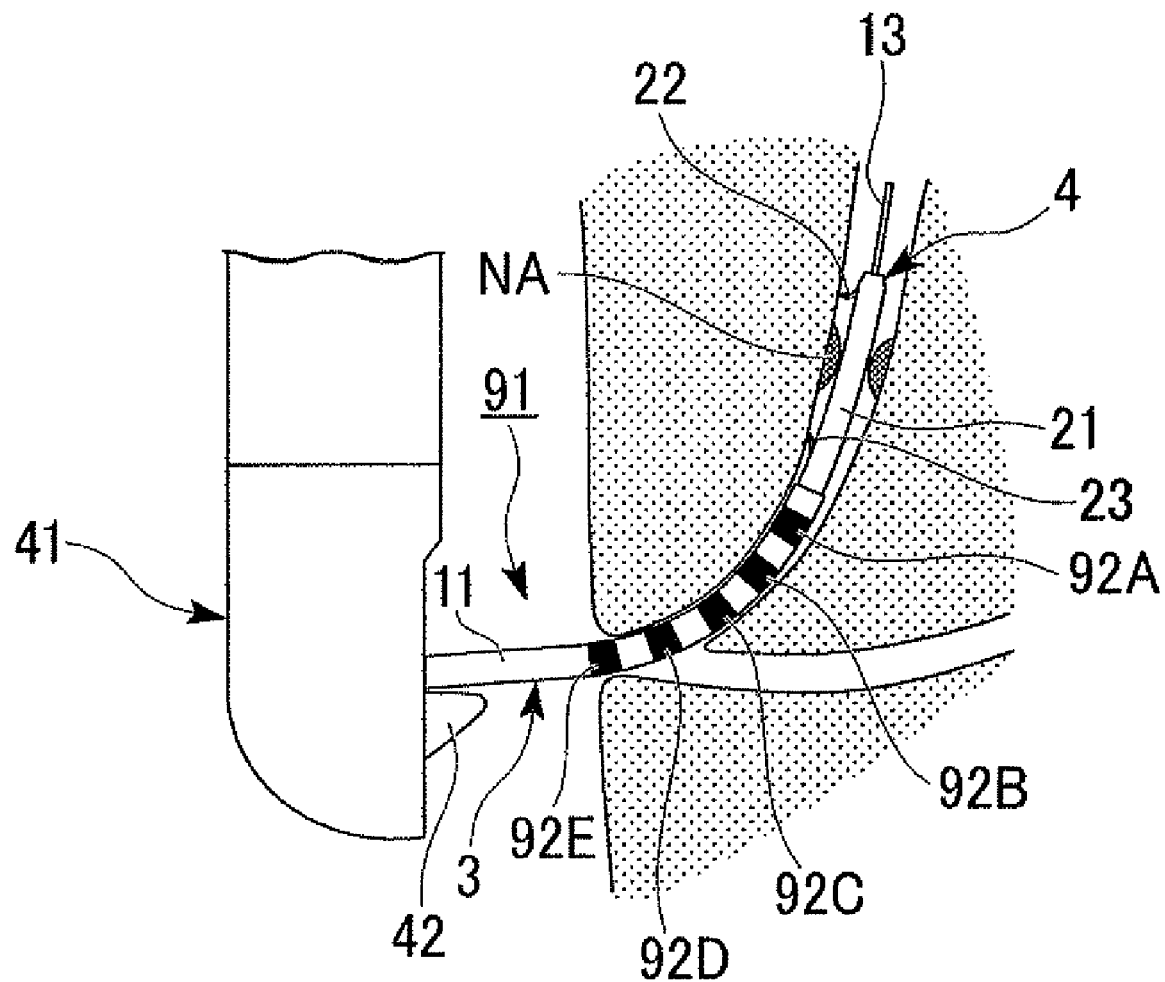
FIG. 34 is a view for explaining the extent of insertion when the length measuring marking closest to the base end side is aligned with the papilla.

When it is acceptable that the length of the grip piece 24 disposed in the duodenum is short, then a length measurement marking that is farther toward the base end side (length measurement marking 92D, 92E, for example) is aligned with the papilla DN, and the stent 4 is released. When the length measurement marking 92E that is the farthest toward the base end side is aligned with the papilla DN, then, in this case, the length of the grip piece 24 that is pulled out into the duodenum becomes the shortest, as shown in FIG. 34.

When it desired to have a longer portion of the grip piece 24 disposed inside the duodenum, then a length measurement marking that is toward the front end (length measurement marking 92A, 92B, 92C for example) is aligned with the papilla DN and the stent 4 is released. By providing multiple length measurement markings 92A-92E, in addition to the effects described above, it is possible to adjust the projecting length of the grip piece 24 while confirming the length using the endoscopic image.

Tenth Embodiment

Figure 35:
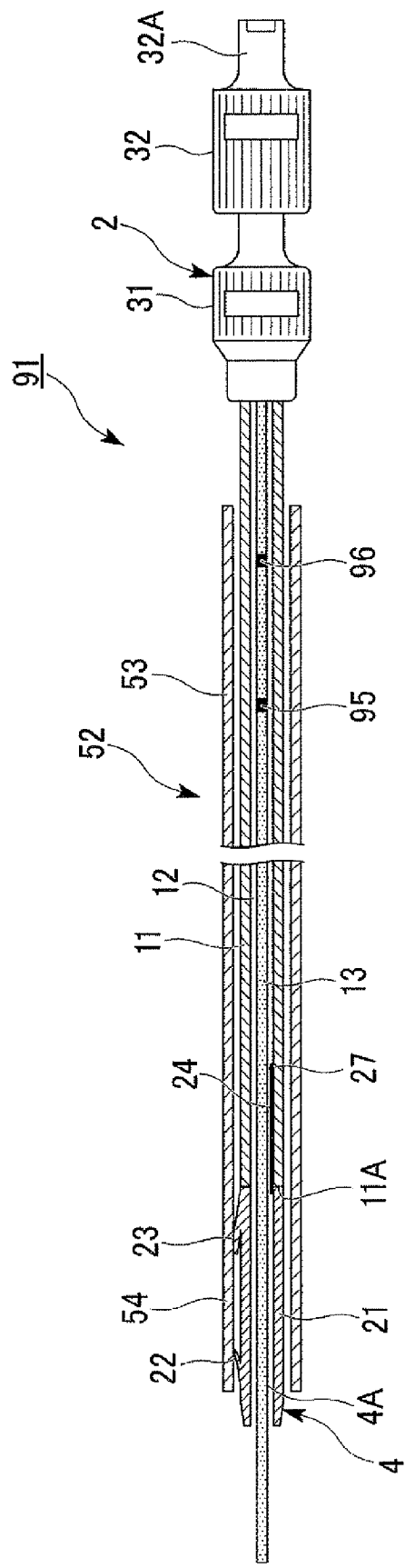
FIG. 35 is a view in which a marking is provided to the base end side of the guide catheter.

As shown in FIG. 35, two types of expelling markings are provided to the base end side of the guide catheter 13 in this stent delivery system 91.

Figure 36:
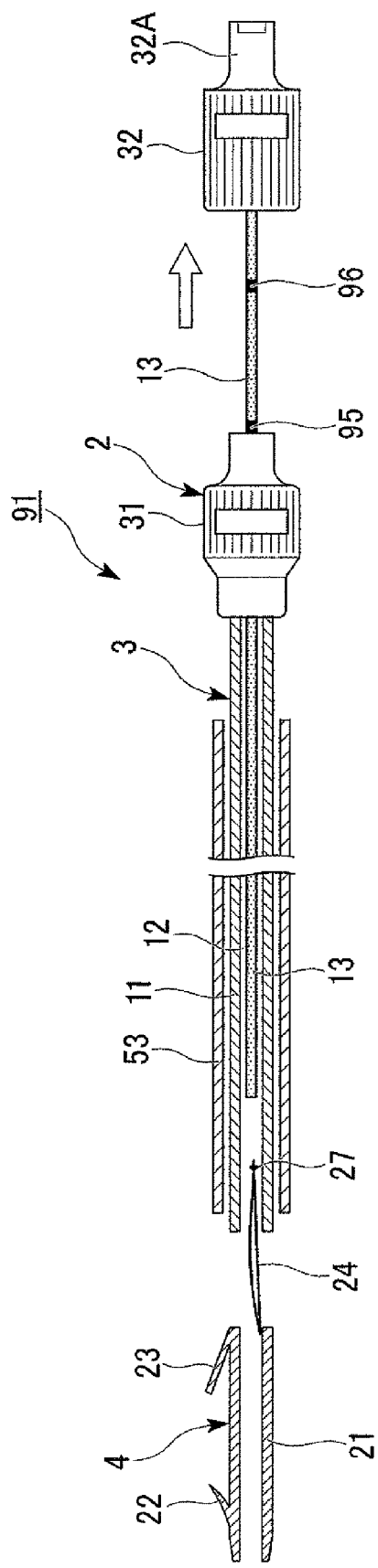
FIG. 36 is a view in which the release marking is aligned with the first base.

The first expelling marking provided toward the front end is a release marking 95. When this release marking 95 is aligned with the base end surface of the first base 31 as shown in FIG. 36, the front end surface of the guide catheter 13 is pulled back farther toward the base end side than the grip piece 24.

Figure 37:
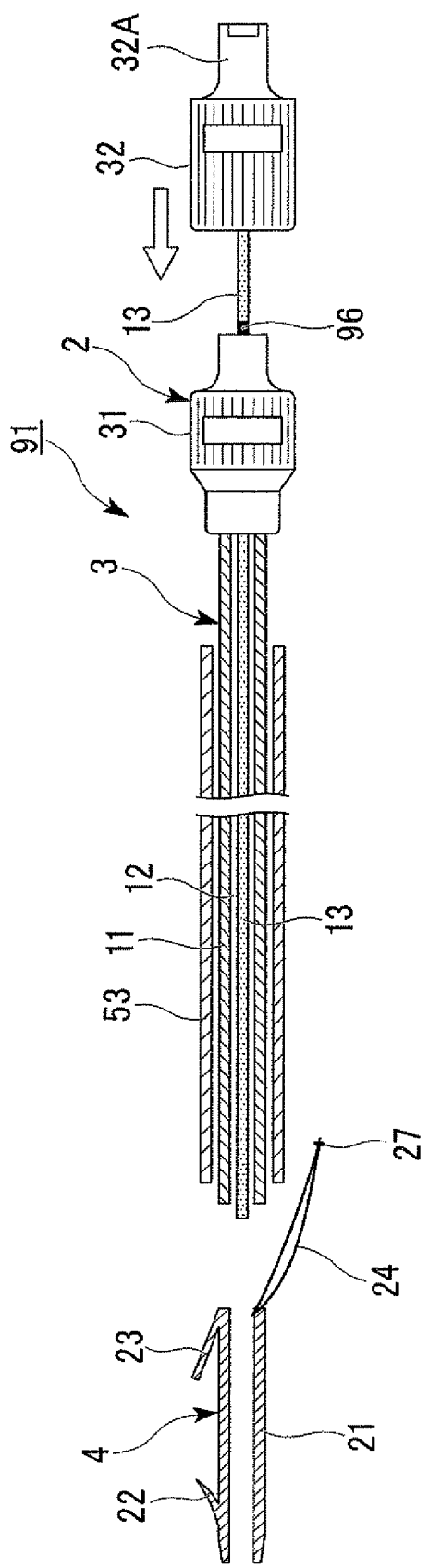
FIG. 37 is a view in which the push-out marking is aligned with the first base.

The second expelling marking provided toward the base end is a push-out marking 96. When this push-out marking 96 is aligned with the base end surface of the first base 31 as shown in FIG. 37, the front end surface of the guide catheter 13 is projected out from the front end of the pusher catheter 11.

When placing the stent 4, the stent 4 is introduced to the stricture site NA. The outer sheath 53 is retracted, allowing the flaps 22,23 of the stent 4 to open. The engagement between the first base 31 and the second base 32 is released, and only the second base 32 is pulled back. The second base 32 is pulled until the release marking 95 appears at the base end surface of the first base 31. The guide catheter 13 is pulled out from the stent 4, and the stent 4 is released. The grip piece 24 is disposed inside the lumen 12 of the pusher catheter 11 once the guide catheter 13 has been pulled out.

Next, the inserted part 3 is pulled back into the duodenum and the second base 32 is pushed in with respect to the first base 31. The second base 32 is pushed in until the push out marking 96 is roughly aligned with the base end surface of the first base 31. The grip piece 24 is pushed out by the front end surface of the guide catheter 13, and is expelled from the pusher catheter 11. As a result, the stent 4 is disposed at the stricture site NA, and the grip piece 24 passes through the papilla DN and is pulled out into the duodenum.

These markings 95,96 serve as the standards for positioning the placement of the stent 4 and the expelling of the grip piece 24, As a result, it becomes possible to carry out the operation of placing the stent 4 more easily.

Note that it is also acceptable to provide a stent holder 15 in place of the outer sheath 53. When pushers 82-84 have been provided to the guide catheter 13, the push-out marking 96 is provided at a position so that the pusher 82-84 will project out from the front end of the pusher catheter 11.

When any of markings 92, 92A-92E are further provided to the side of the pusher catheter 11, the end of the grip piece 24 can be expelled into the duodenum with certainty.

Eleventh Embodiment

Figure 38:
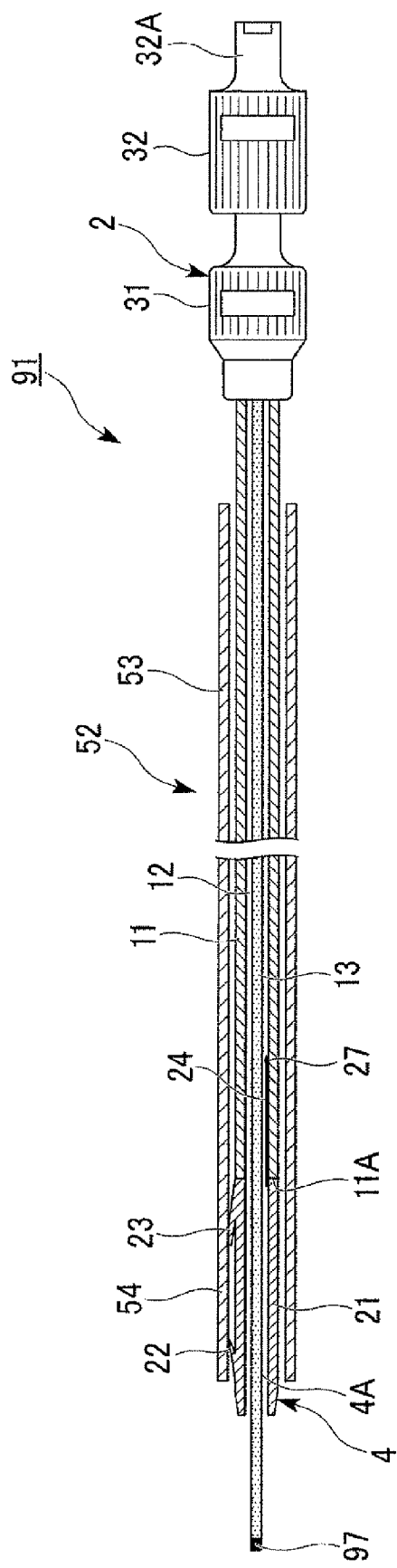
FIG. 38 is a view in which a marking is provided to the front end of the guide catheter.

As shown in FIG. 38, a guide marking 97 is provided to the front end of the guide catheter 13 in this stent delivery system 91. The guide marking 97 has a color or pattern that can be confirmed via the endoscopic image.

Figure 39:
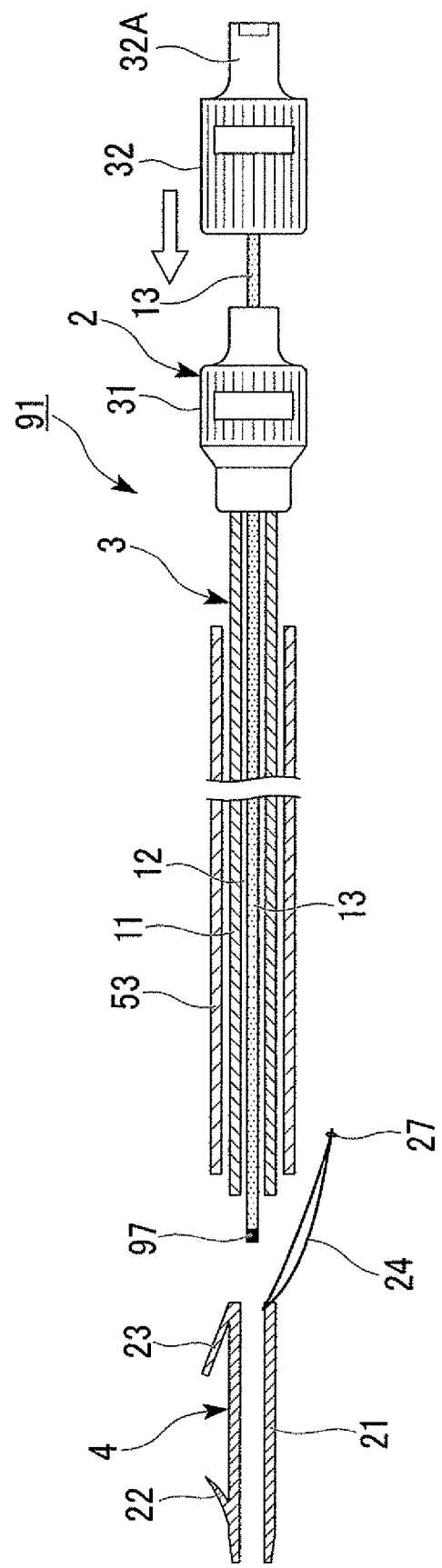
FIG. 39 is a view in which the marking has been projected out so that it can be confirmed with the endoscope.

The operation when placing the stent 4 is the same as that performed in the second embodiment. When pushing out the grip piece 24 using the guide catheter 13, the guide catheter 13 is advanced until the guide marking 97 can be confirmed via the endoscopic image, as shown in FIG. 39. The grip piece 24 is then pushed out from the pusher catheter 11 using the guide catheter 13.

The guide marking 97 can be easily confirmed via endoscopic visualization. Thus, the grip piece 24 is expelled from the pusher catheter 11 into the duodenum with certainty as long as the guide catheter 13 is pushed out until the guide marking 97 appears. Thus, even in the case where it is difficult to confirm the grip piece 24 using the endoscopic image, the grip piece 24 can be expelled with certainty by employing this guide marking 97.

In the case where providing a pusher 82, brush 83, or cut-out 84, it is sufficient to provide these at a position where it is deemed that these pushers will definitely push out the grip piece 24, i.e., at a position where the pusher will sufficiently project out from the contact surface 11A of the pusher catheter 11, for example.

Twelfth Embodiment

Figure 40:
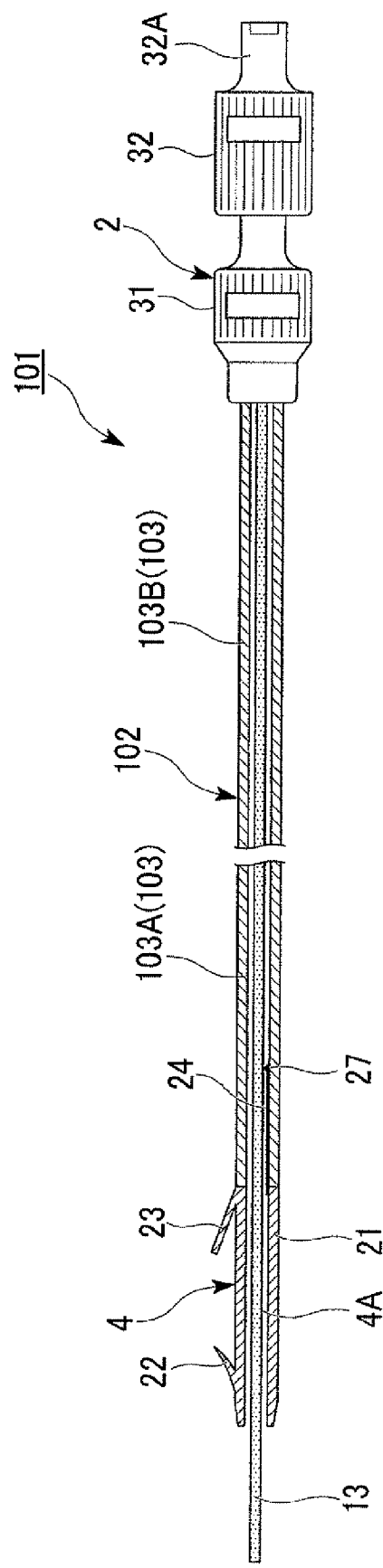
FIG. 40 is a view showing a design in which the pusher catheter is connected to a first part which has excellent flexibility, and a second part that is extremely strong.
Figure 41:
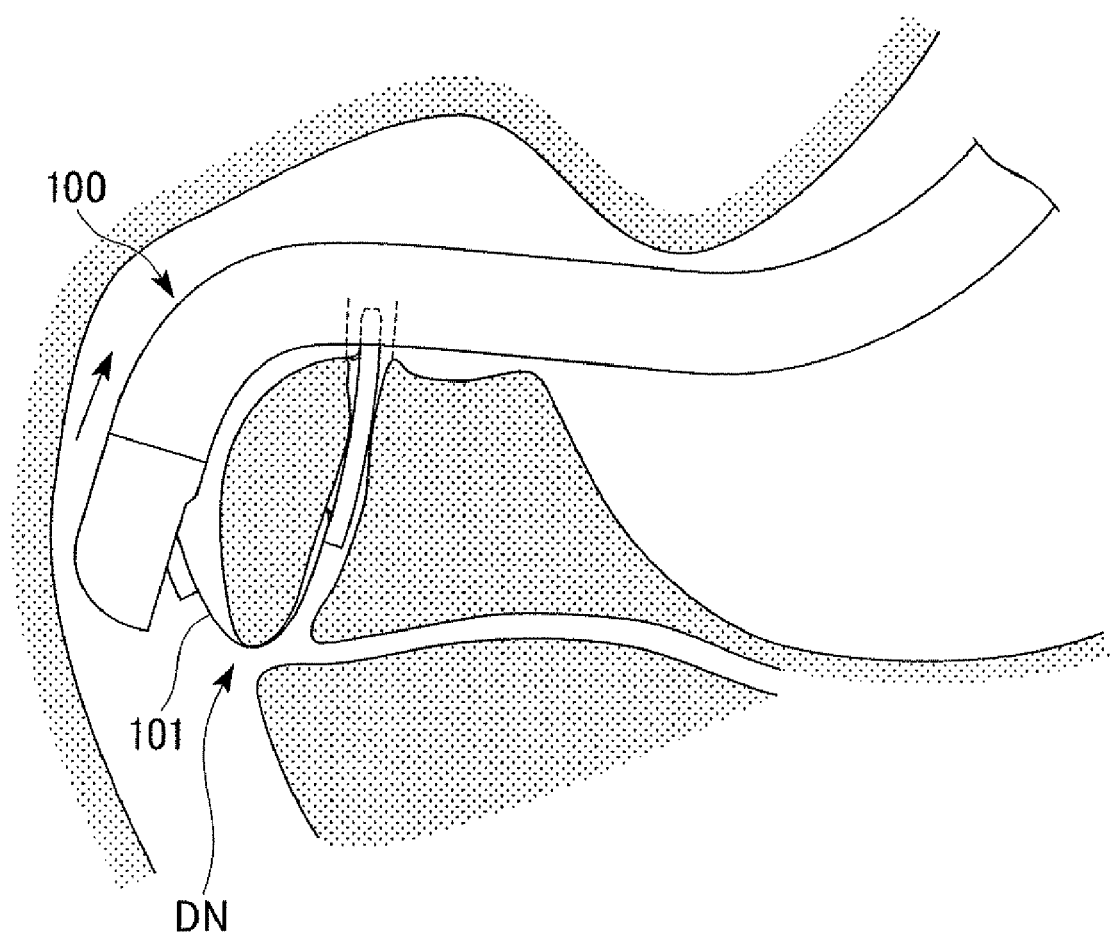
FIG. 41 is a view showing the operation when expelling the grip piece in a conventional stent delivery system.

As shown in FIG. 40, in this stent delivery system 101, the pusher catheter 103 of the inserted part 102 is designed such that a first part 103A on the front end and a second part 103B on the base end are connected. The first part 103A has greater flexibility than the second part 103B. The second part 103B has greater strength than the first part 103A. These two parts 103A, 103B are formed from different materials for example, and are connected via an adhesive or the like. The length of the first part 103A is from 5 cm to 30 cm. This length is roughly equivalent to the length of the front part of the endoscope 41 that can be bent via angle manipulation.

The operation when placing the stent 4 is the same as that described above. The second part 103B is highly strong and thus difficult to bend. As a result, it is easily passed through endoscope 41. The portion of the endoscope 41 that is inserted from the stomach into the duodenum is greatly bent. It is the first part 103A of the pusher catheter 103 that is passed within this region, so that the catheter bends easily in response to the shape of the endoscope 41. The insertion properties are thus excellent.

When guiding the stent 4 to the stricture site NA, or when pushing out the grip piece 24 using the guide catheter 13, etc., a compressive force acts on the pusher catheter 103. Since the second part 103B, which has little flexibility, comprises a large proportion of the entire length of the pusher catheter 103, this limits incongruity between the amount of manipulation at the hand-held side and the amount of change that results at the front end. This pusher catheter 103 can be incorporated into any of the embodiments previously explained.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A stent delivery system for placing a stent inside a body cavity following insertion into an endoscope, said stent delivery system comprising:
   a pusher catheter which is flexible, the pusher catheter comprising:
      a stent housing on a front end thereof, and
      an inner circumferential surface defining a pusher catheter lumen;
   a guide catheter configured to be inserted through the pusher catheter lumen in a freely advancing and retracting manner; and
   a stent which is disposed in the stent housing, the stent comprising:
      a cylindrical stent main body into which the guide catheter is capable of being inserted, and
      a grip piece that is attached so as to extend from a base end of the stent main body, the grip piece comprising a long narrow member that is pliable, wherein,
   the inner circumferential surface of the pusher catheter and an outer circumferential surface of the guide catheter define a space within which the grip piece of the stent is housed so as to extend from the base end of the stent main body to a base end side of the pusher catheter in an axial direction of the pusher catheter between an inner wall of the pusher catheter and an outer wall of the guide catheter in a state where the guide catheter is inserted through the pusher catheter lumen and the stent main body,
   the stent housing has an outer diameter larger than that of the pusher catheter and a lumen in which an inner diameter thereof is larger than an outer diameter of the stent main body,
   the stent further comprising at least one flap formed on a side surface of the stent main body so as to open naturally toward a radially outward direction of the stent main body, the at least one flap being elastically deformable so as to be folded toward the stent main body under the application of external force, and
   the stent is housed in the lumen of the stent housing in a state where the flap comes into contact with the stent main body.

2. The stent delivery system according to claim 1, wherein the grip piece further comprises an expanded part, at least a portion of which has a diameter that is larger than the long narrow member, and which is capable of being pushed out by the guide catheter.

3. The stent delivery system according to claim 1, further comprising a pusher operatively connected to the guide catheter, the pusher having an outer diameter that is larger than an outer diameter of the guide catheter and that is equal to or less than a diameter of the pusher catheter lumen,
   wherein the pusher is configured to be moved by the guide catheter to contact the grip piece of the stent and to push the grip piece relative to the pusher catheter lumen.

4. The stent delivery system according to claim 1, wherein at least one of the guide catheter and the pusher catheter includes a marking to permit visual recognition via an image acquired by the endoscope, the marking being provided at a position that is within a specific distance from a base end of the grip piece in a state where the stent is housed in the stent housing, the guide catheter is inserted through the pusher catheter and the stent main body, and the grip piece is disposed in the space defined by the inner circumferential surface of the pusher catheter and the guide catheter.

5. The stent delivery system according to claim 1, wherein the guide catheter includes at least one of:
   a first expelling marking provided at a first position on a base end side of the guide catheter, the first expelling marking providing a visual indication of contact between the guide catheter and the grip piece, with pushing out of the grip piece beginning thereafter, and
   a second expelling marking provided at a second position on the base end side of the guide catheter, the second expelling marking providing a visual indication of completion of expulsion of the grip piece to the outside of the pusher catheter.

6. The stent delivery system according to claim 1, wherein the grip piece comprises a pliable thread through a hole that is formed in the base end of the stent main body.

* * * * *